United States Patent [19]

Endo et al.

[11] Patent Number: 5,739,083
[45] Date of Patent: Apr. 14, 1998

[54] PYRAZOLE DERIVATIVES AND INSECTICIDAL COMPOSITIONS CONTAINING THE DERIVATIVE AS ACTIVE COMPONENT

[75] Inventors: Yoshinori Endo; Hiroshi Fujishima; Keizaburo Murai; Tetsuji Miyata; Shigekazu Wakisaka; Yasuhiro Sasama, all of Tokushima, Japan

[73] Assignee: Otsuka Kagaku Kabushiki Kaisha, Osaka, Japan

[21] Appl. No.: 849,472

[22] PCT Filed: Oct. 9, 1996

[86] PCT No.: PCT/JP96/02946

§ 371 Date: Jun. 10, 1997

§ 102(e) Date: Jun. 10, 1997

[87] PCT Pub. No.: WO97/13756

PCT Pub. Date: Apr. 17, 1997

[30] Foreign Application Priority Data

Oct. 13, 1995 [JP] Japan .................. 7-292164

[51] Int. Cl.$^6$ .................. A61K 31/415; C07D 231/20
[52] U.S. Cl. .................. 504/282; 546/276.1; 548/366.4; 548/366.1; 548/367.4; 548/368.1; 548/370.1; 548/370.4; 548/371.1
[58] Field of Search .................. 548/370.4, 366.1; 504/282

[56] References Cited

PUBLICATIONS

WO 92/02509, Feb. 1992, Mischke et al.
Brunner et al, Chemical Abstracts, vol. 126 No. 144273 (1997).

*Primary Examiner*—Robert W. Ramsuer
*Attorney, Agent, or Firm*—Kubovcik & Kubovcik

[57] ABSTRACT

A pyrazole derivative represented by the formula (1) is low in toxicity and persistence and yet has an extremely high insecticidal efficacy

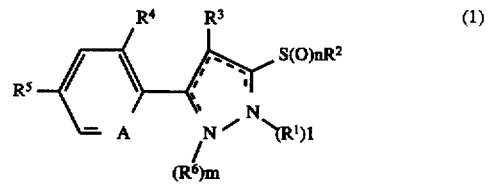

wherein A is CH, N or C-halogen atom, $R^1$ is hydrogen atom, lower alkyl, lower haloalkyl, benzyl or phenyl, $R^2$ is lower alkyl, lower haloalkyl, lower alkenyl, lower alkynyl, benzyl or phenyl, $R^3$ is hydrogen atom, a halogen atom lower alkyl, lower haloalkylthio, phenyl, cyano, nitro or amino, $R^4$ is halogen atom, $R^5$ is lower haloalkyl, $R^6$ is hydrogen atom, lower alkyl, lower haloalkyl or benzyl, $R^1$ and $R^6$ being not hydrogen atoms at the same time, l is 0 or 1, m is 0 or 1 and n is a number of 0 to 2.

12 Claims, No Drawings

PYRAZOLE DERIVATIVES AND INSECTICIDAL COMPOSITIONS CONTAINING THE DERIVATIVE AS ACTIVE COMPONENT

This application is a 371 of PCT/JP96/02946 filed Oct. 9, 1996.

TECHNICAL FIELD

The present invention relates to pyrazole derivatives and insecticidal compositions containing the derivative as their active component.

BACKGROUND ART

With insecticides in use for many years, pest insects have acquired resistance in recent years and become difficult to control with conventional insecticides. Some of the insecticides have a high toxicity and some are persistent, disturbing the ecological system. Accordingly it is expected to develop novel insecticides having a low toxicity and less persistence.

Up to date, some types of pyrazole derivatives are known to have herbicidal activity. For example, JP-A-163063/1991 discloses 3-phenyl-5-alkylsulfenylpyrazoles. 5-Phenyl-3-alkylsulfenylpyrazoles are also disclosed in JP-A-509103/1993. However, no studies whatever have been conducted on the insecticidal activity of these compounds and analogues thereof.

An object of the present invention is to provide novel insecticides which are low in toxicity and persistence and yet have an extremely high insecticidal efficacy.

DISCLOSURE OF THE INVENTION

The present invention provides pyrazole derivatives represented by the formula (1), and an insecticidal composition comprising the derivative as its active component

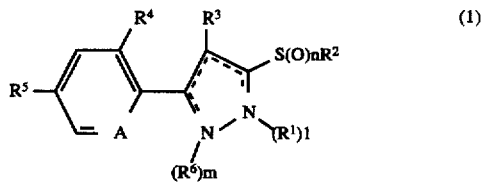

wherein A is CH, N or C-halogen atom, $R^1$ is hydrogen atom, lower alkyl, lower haloalkyl, benzyl or phenyl, $R^2$ is lower alkyl, lower haloalkyl, lower alkenyl, lower alkynyl, benzyl or phenyl, $R^3$ is hydrogen atom, a halogen atom, lower alkyl, lower haloalkylthio, phenyl, cyano, nitro or amino, $R^4$ is halogen atom, $R^5$ is lower haloalkyl, $R^6$ is hydrogen atom, lower alkyl, lower haloalkyl or benzyl, $R^1$ and $R^6$ being not hydrogen atoms at the same time, 1 is 0 or 1, m is 0 or 1 and n is a number of 0 to 2.

The inventors of the present invention have conducted detailed research on the insecticidal activity of pyrazole derivatives. Consequently, they have found that the pyrazole derivatives of the formula (1) are very useful compounds having very high insecticidal activity but almost no injury to mammals, fishes, crustaceans and beneficial insects such as honeybees and accomplished the present invention.

When used at a low dose or concentration, the compounds of the present invention effectively control pest insects of the orders Orthoptera, Hemiptera, Lepidoptera, Coleoptera, Hymenoptera, Diptera and Isoptera, mites and lice. More specific examples of harmful organisms controllable with the compound of the invention are agricultural harmful insects such as *Nephotettix cincticeps, Nilaparvata lugens, Myzus persicae, Epilachna vigintioctopunctata, Spodoptera litura, Cnaphalocrocis medinalis* and *Plutlla xylostella*, spider mites such as *Tetranychus urticae, Panonychus citri* and *Tetranychus kanzawai*, sanitary insect pest such as *Culex pipfens pallens, Musca domestica, Blattella germanica*, ants, fleas and lice, insects harmful to storage such as *Sitophilus oryzae, Tribolium castaneum* and *Ephestia cautella*, household harmful insects such as termites, insects harmful to cattle such as mites, fleas and lice, household mites such as acarid mites, house dust mites, cheyletid mites, and mollusks such as slugs and snails.

The compounds (1) of the invention include the compounds (1A) and (1B) given below

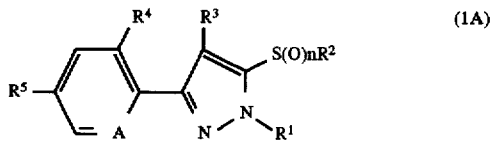

wherein A and $R^1$ to $R^5$ are the same as above

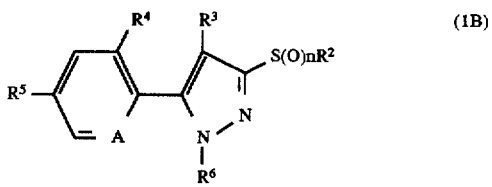

wherein A and $R^2$ to $R^6$ are the same as above.

Examples of each group shown by A, $R^1$~$R^6$ in the formula (1) are as follows.

Halogen atoms include fluorine, chlorine, bromine and iodine atoms. Lower alkyl groups are preferably straight-chain or branched alkyl having 1 to 6 carbon atoms such as methyl, ethyl, n-propyl, isopropyl, n-butyl, isobutyl, tert-butyl, pentyl, isopentyl and hexyl. Lower haloalkyl groups are preferably straight-chain or branched haloalkyl having 1 to 6 carbon atoms in which the above halogen atom is substituted on the above alkyl group. Lower alkenyl groups are preferably straight-chain or branched alkenyl having 2 to 6 carbon atoms such as vinyl, propenyl, butenyl and hexenyl. Lower alkynyl groups are preferably straight-chain or branched alkynyl having 2 to 6 carbon atoms such as acetylenyl and propargyl. Lower haloalkylthio groups are preferably straight-chain or branched haloalkylthio having 1 to 6 carbon atoms such as those in which the above halogen atom is substituted on methylthio, ethylthio, n-propylthio, n-butylthio and hexylthio.

Among the present compounds of the formula (1) are especially preferable the following compounds.

Compound of the formula (1) wherein A is C—Cl, n is 0, $R^1$ and $R^2$ are both lower alkyl, $R^3$ is hydrogen atom and $R^5$ is trifluoromethyl group.

Compound of the formula (1) wherein A is C—Cl, n is 0, $R^1$ and $R^2$ are both lower alkyl, $R^3$ is chlorine atom and $R^5$ is trifluoromethyl group.

Compound of the formula (1) wherein A is C—Cl, n is 1, $R^1$ and $R^2$ are both lower alkyl, $R^3$ is hydrogen atom and $R^5$ is trifluoromethyl group.

Compound of the formula (1) wherein A is C—Cl, n is 2, $R^1$ and $R^2$ are both lower alkyl, $R^3$ is hydrogen atom and $R^5$ is trifluoromethyl group.

Compound of the formula (1) wherein A is C—Cl, n is 0, $R^1$ and $R^2$ are both lower alkyl, $R^3$ is cyano group and $R^5$ is trifluoromethyl group.

Compound of the formula (1) wherein A is C—Cl, n is 2, $R^1$ and $R^2$ are both lower alkyl, $R^3$ is nitro group and $R^5$ is trifluoromethyl group.

Compound of the formula (1) wherein A is C—Cl, n is 2, $R^1$ and $R^2$ are both lower alkyl, $R^3$ is amino group and $R^5$ is trifluoromethyl group.

Compound of the formula (1) wherein A is C—Cl, n is 2, $R^1$ and $R^2$ are both lower alkyl, $R^3$ is lower haloalkylthio group and $R^5$ is trifluoromethyl group.

Compound of the formula (1) wherein n is 0, $R^2$ is propargyl group and $R^5$ is trifluoromethyl group.

Compound of the formula (1) wherein n is 0, $R^2$ is trifluoromethyl group and $R^5$ is trifluoromethyl group.

The compound of the formula (1A) of the invention can be prepared by various processes, for example, by the following synthetic process.

(Process A)

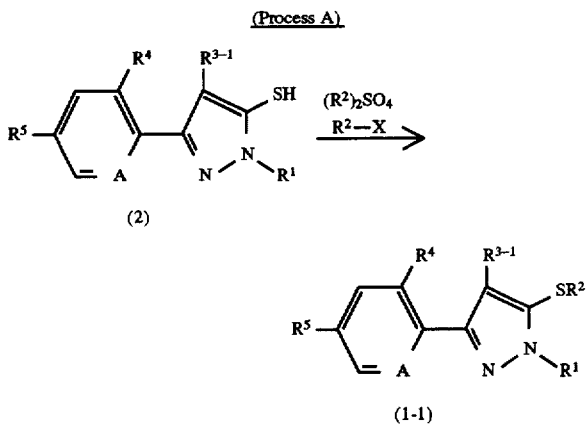

wherein $R^1$, $R^2$, $R^4$, $R^5$ and A are the same as above $R^{3-1}$ is a hydrogen atom, lower alkyl or phenyl, and X is halogen atom.

As represented above, a pyrazole represented by the formula (2) is reacted with an alkyl halide and/or dialkyl sulfate in an inert solvent in the presence of a base to give a compound of the invention represented by the formula (1-1).

Examples of alkyl halides used in the process A are alkyl halides such as methyl iodide, ethyl iodide, propyl iodide, trifluoromethyl iodide, methyl bromide, ethyl bromide and methyl chloride; alkenyl halides such as allyl bromide and methallyl chloride; alkynyl halides such as propargyl bromide; benzyl halides such as benzyl bromide and benzyl chloride. Examples of dialkyl sulfates are alkyl sulfates such as dimethyl sulfate and diethyl sulfate.

Examples of bases used in the process A are alkali metal alkoxides such as sodium methoxide, sodium ethoxide and potassium tert-butoxide; alkali metal hydroxides such as sodium hydroxide and potassium hydroxide; alkali metal carbonates such as sodium carbonate and potassium carbonate; organic bases such as triethylamine and pyridine; alkali metal hydrides such as sodium hydride. The amount of the base is preferably 1 to 10 equivalents per equivalent of pyrazole of the formula (2).

In the reaction, alkyl halide and/or dialkyl sulfate are/is used each in an amount of preferably 1 to 10 equivalents per equivalent of mercaptopyrazole of the formula (2).

Examples of solvents favorable to use in the process A are halogenated hydrocarbons such as carbon tetrachloride, chloroform and 1,2-dichloroethane; aromatic hydrocarbons such as benzene and toluene; ethers such as diethyl ether, tetrahydrofuran and 1,4-dioxane; ketones such as acetone; amides such as dimethyl formamide and hexamethyl phosphoric triamide (HMPA); dimethyl sulfoxide; or mixture of these solvents. It is possible to use a mixture of the solvent and water as required, or to add a quaternary ammonium salt such as tetra-n-butylammonium bromide as a catalyst as required.

Although not limited specifically, the reaction temperature is usually in the range of at least −30° C. to the boiling point of the solvent used.

The pyrazole represented by the formula (2) and to be used as the starting material in the process A can be prepared, for example, by the following reaction.

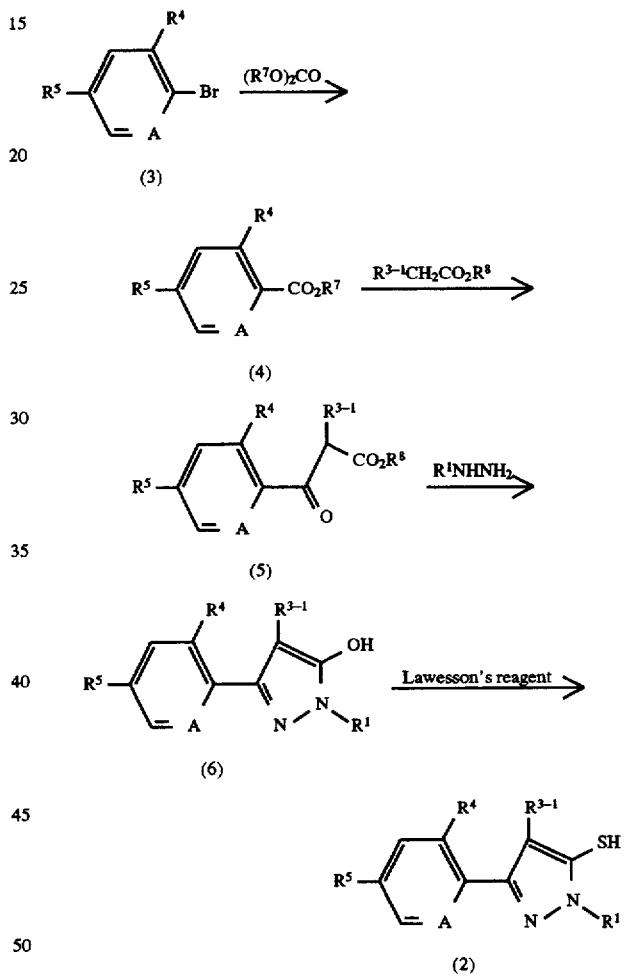

wherein $R^1$, $R^2$, $R^{3-1}$, $R^4$, $R^5$ and A are the same as above, $R^7$ and $R^8$ are the same or different and are lower alkyl.

More specifically, the pyrazole represented by the formula (2) can be obtained by the reaction of a compound represented by the formula (3) with a dialkyl carbonate to prepare a compound represented by the formula (4), by the reaction of the compound with an ester represented by the formula $R^{3-1}CH_2CO_2R^8$ to obtain a β-ketoester compound represented by the formula (5), by the reaction of the ketoester compound with a hydrazine derivative to obtain a pyrazole derivative represented by the formula (6) and thereafter by the reaction of the derivative with Lawesson's reagent [2,4-bis(methoxyphenyl)-1,3-dithia-2,4-diphosphetane-2,4-disulfide].

The β-ketoester compound represented by the formula (5) can also be prepared according to the following reaction formula.

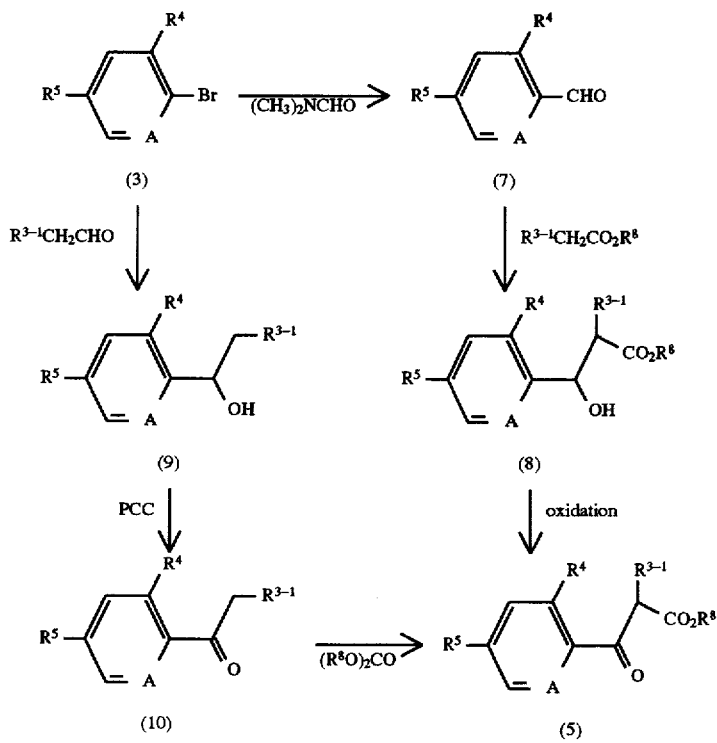

wherein A, $R^{3-1}$, $R^4$, $R^5$ and $R^8$ are the same as above.

More specifically, the β-ketoester compound represented by the formula (5) can be obtained by the reaction of a compound represented by the formula (3) with a formamide compound to prepare a compound represented by the formula (7), converting the compound to a compound represented by the formula (8) by the Reformatskii reaction and further by the reaction of the compound (8) with an oxidizing agent such as manganese dioxide or chromic acid salt, or by the reaction of a compound represented by the formula (3) with an aldehyde to prepare an alcohol represented by the formula (9), subsequently by the reaction of the alcohol with pyridinium chlorochromate (PCC) to prepare a compound represented by the formula (10) and thereafter by the reaction of the compound with a dialkyl carbonate represented by the formula $(R^8O)_2CO$.

A compound (5-1) corresponding to the β-ketoester compound of the formula (5) wherein $R^{3-1}$ is hydrogen can be prepared also by the following reaction

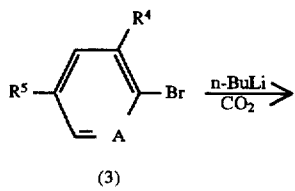

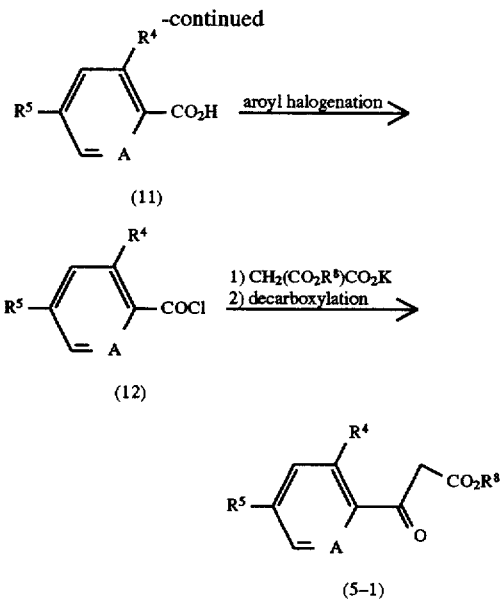

wherein A, $R^4$, $R^5$ and $R^8$ are the same as above.

More specifically stated, the compound represented by the formula (5-1) can be prepared by the reaction of carbon dioxide with a compound represented by the formula (3) to obtain a compound represented by the formula (11), thereafter by the reaction of the compound with a halogenating agent such as thionyl chloride to obtain an acid halide represented by the formula (12), by the reaction of the halide with an esterifying agent such as the potassium salt of monoethyl malonate and decarboxylating the resulting product.

(Process B)

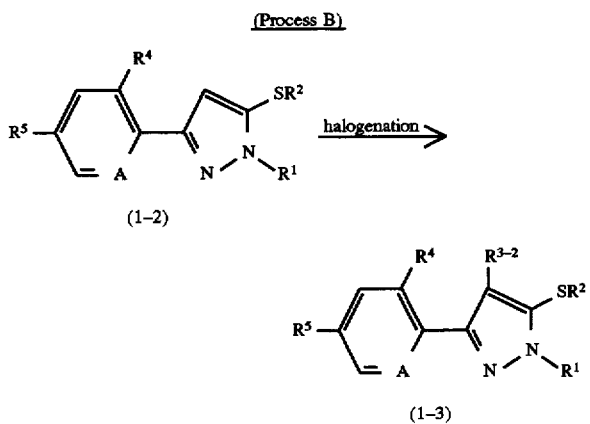

wherein $R^1$, $R^2$, $R^4$, $R^5$ and A are the same as above. $R^{3-2}$ is halogen atom.

A compound of the invention represented by the formula (1-2) is reacted with a halogenating agent in a suitable inert solvent to give a compound of the invention represented by the formula (1-3).

A compound of the invention represented by the formula (1-2) is reacted with a halogenating agent in a suitable inert solvent to give a compound of the invention represented by the formula (1-3).

Examples of halogenating agents used in the process B are chlorine, bromine, N-bromosuccinimide, N-chlorosuccinimide, sulfuryl chloride and sulfuryl bromide. The amount of the halogenating agent is preferably 1 to 10 equivalents per equivalent of the compound of the formula (1-2).

Examples of inert solvents suitable to use in the process B are hydrocarbon halides such as carbon tetrachloride, chloroform, methylene chloride and 1,2-dichloroethane; amides such as dimethyl formamide; carbon disulfide; nitrobenzene; acetic acid; or mixture of these solvents.

Although not limited specifically, the reaction temperature is usually in the range of at least −30° C. to the boiling point of the solvent used.

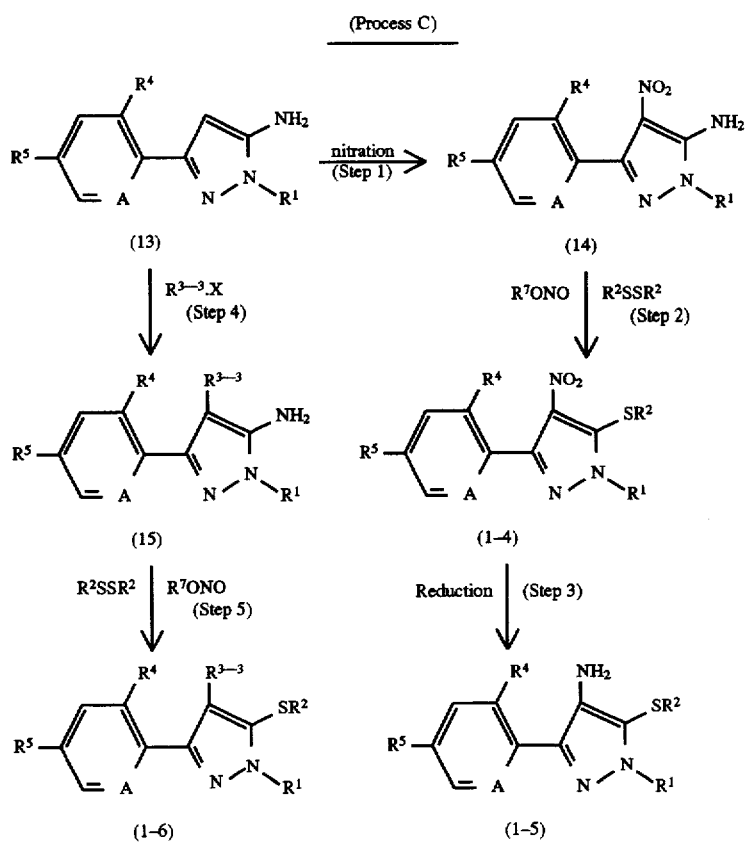

wherein $R^1$, $R^2$, $R^4$, $R^5$, $R^7$, A and X are the same as above, $R^{3-3}$ a is lower alkylthio or lower haloalkylthio.

A compound of the invention represented by the formula (1-4) can be prepared by the above reaction, i.e., by the nitration of an aminopyrazole represented by the formula (13) in a suitable inert solvent to a nitropyrazole represented by the formula (14) in step 1, and further by the reaction of the nitropyrazole represented by the formula (14) with an alkyl nitrite in the presence of a dialkyl disulfide in step 2. A compound of the invention represented by the formula (1-5) can be prepared by the reduction of the nitro group of the compound (1-4) further in step 3.

A compound of the invention represented by the formula (1-6) can be prepared by the reaction of an aminopyrazole represented by the formula (13) with a sulfenyl halide in a suitable inert solvent to obtain a sulfenylpyrazole represented by the formula (15) in step 4, and further by the reaction of the pyrazole with an alkyl nitrite in the presence of a dialkyl disulfide in step 5.

Examples of solvents suitable to use in the process C, step 1 are hydrocarbon halides such as methylene chloride and 1,2-dichloroethane and acid anhydrides such as acetic anhydride, besides those wherein concentrated sulfuric acid is used as the component to be mixed with other acid.

Examples of useful nitrating agents are nitric acid, fuming nitric acid, nitric acid salts of alkali metals including potassium nitrate and mixed acid. The amount of nitrating agent to be used for the reaction is preferably 1 to 10 equivalents per equivalent of the pyrazole represented by the formula (13).

Although not limited specifically, the reaction temperature is usually in the range of at least 0° C. to the boiling point of the solvent used. The reaction usually requires about 1 to about 24 hours for completion.

Examples of solvents suitable to use in the process C, step 2 or 5 are hydrocarbon halides such as carbon tetrachloride, chloroform, methylene chloride and 1,2-dichloroethane; ethers such as diethyl ether, tetrahydrofuran and 1,4-dioxane; and nitriles such as acetonitrile.

Examples of dialkyl disulfides favorable to use in the step 2 or 5 are lower dialkyl disulfides such as dimethyl disulfide and diethyl disulfide; lower dihaloalkyl disulfides such as ditrifluoromethyl disulfide; and disulfides such as dibenzyl disulfide and diphenyl disulfide. Examples of alkyl nitrites are lower alkyl nitrites such as methyl nitrite, isoamyl nitrite and t-butyl nitrite.

The amount of the alkyl nitrite is preferably 1 to 5 equivalents per equivalent of pyrazole of the formula (14) or (15). The amount of the dialkyl disulfide is preferably 1 to 10 equivalents per equivalent of pyrazole of the formula (14) or (15).

Although not limited specifically, the reaction temperature is usually in the range of at least −30° C. to the boiling point of the solvent used. The reaction time is usually about 1 to about 24 hours for completion.

Examples of solvents favorable to use in the process C, step 3 are alcohols such as methanol and ethanol; esters such as ethyl acetate and butyl acetate; ethers such as diisopropyl ether, dioxane, tetrahydrofuran and ethylene glycol dimethyl ether; ketones such as acetone and cyclohexane; water; or mixture of these solvents.

The reducing agent is, for example, hydrogen, while examples of catalysts useful for catalytic reduction are palladium carbon, platinum carbon, palladium chloride and palladium oxide. The amount of reducing agent for the reaction is preferably 3 to 4 equivalents per equivalent of the pyrazole represented by the formula (1-4). When to be used, the reduction catalyst is used usually in an amount of 0.1 to 100 wt. %, preferably 0.5 to 10 wt. %, based on the pyrazole represented by the formula (1-4).

The reaction pressure, which is not limited particularly, is usually in the range of about 1 to about 10 atm. to ensure progress of the reaction. Although not limited particularly, the reaction temperature is usually in the range of not lower than −30° C. to the boiling point of the solvent used. The reaction usually requires about 0.1 to about 24 hours for completion.

The reducing reaction of the step may be conducted by a wide variety of known processes including one wherein the nitro group is reduced to an amino group in the presence of iron or tin in a mineral acid such as hydrochloric acid or in acetic acid, or one wherein a metal hydride such as lithium aluminum hydride is used.

The pyrazole represented by the formula (13) used as the starting material in the process C can be prepared, for example, by the following reaction.

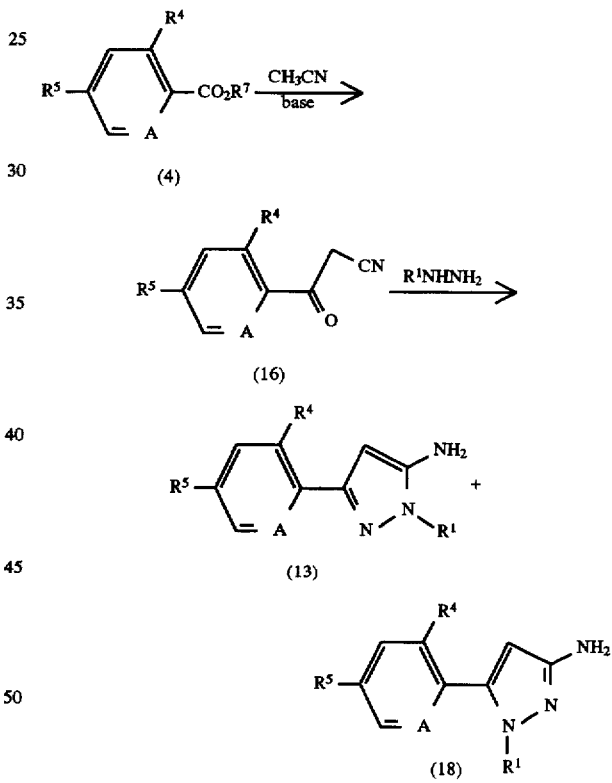

wherein $R^1$, $R^4$, $R^5$, $R^7$ and A are the same as above.

Stated more specifically, pyrazoles represented by the formula (13) and the formula (18) can be produced by the reaction of a compound represented by the formula (4) with acetonitrile in the presence of a base to obtain β-ketonitrile compound represented by the formula (16) and further by the reaction of the nitrile compound with a hydrazine derivative. The proportions of the compound (13) and the compound (18) to be formed can be suitable adjusted. The compound (13) and the compound (18) can be readily isolated from each other.

(Process D)

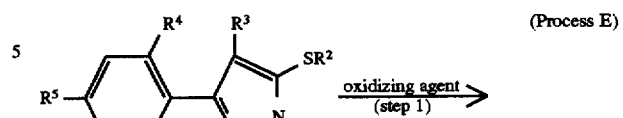

(Process E)

wherein $R^1$, $R^2$, $R^4$, $R^5$ and A are the same as above $R^{3-4}$ is hydrogen atom, cyano, lower alkyl or phenyl.

A compound of the invention represented by the formula (1-7) can be prepared by the above reaction, i.e., by the reaction of a ketene dithioacetal derivative of acetophenone or pyridyl methyl ketone derivative, represented by the formula (17), with a hydrazine derivative in a suitable inert solvent.

Examples of solvents suitable to use in the process D are halogenated hydrocarbons such as carbon tetrachloride, chloroform and 1,2-dichloroethane; aromatic hydrocarbons such as benzene and toluene; ethers such as diethyl ether, tetrahydrofuran and 1,4-dioxane; amides such as dimethyl formamide and HMPA; dimethyl sulfoxide; or mixture of these solvents.

Examples of hydrazines are alkylhydrazines such as methylhydrazine and ethylhydrazine; haloalkylhydrazines such as monofluoromethylhydrazine; benzylhydrazine; and phenylhydrazine.

For the reaction of the compound of the formula (17) with the hydrazine, preferably 1 to 5 equivalents of the latter is used per equivalent of the former.

Although not limited particularly, the reaction temperature is usually in the range of not lower than −30° C. to the boiling point of the solvent used. The reaction usually requires about 0.1 to about 24 hours for completion.

The compound represented by the formula (17) used as the starting material in the process D can be prepared, for example, by the following reaction.

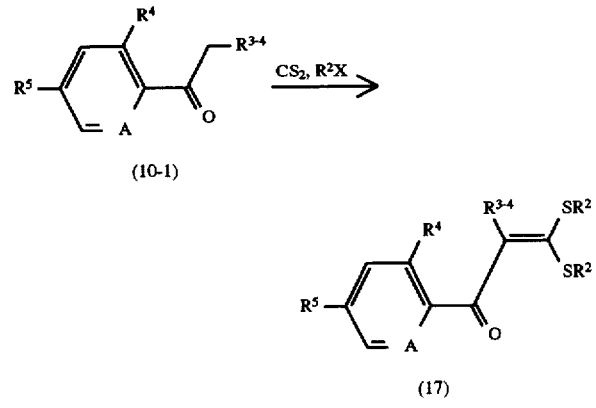

wherein $R^2$, $R^4$, $R^5$, $R^{3-4}$, A and X are the same as above.

More specifically, the compound of the formula (17) can be prepared by the reaction of a ketone derivative represented by the formula (10-1) with carbon disulfide and an alkyl halide.

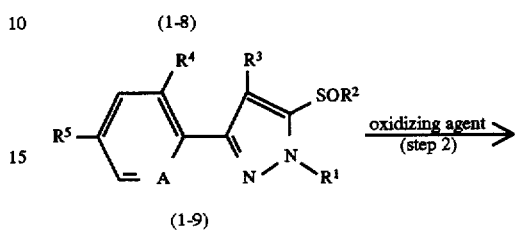

wherein $R^1$, $R^2$, $R^3$, $R^4$, $R^5$ and A are the same as above.

A compound of the invention represented by the formula (1-9) can be obtained by the above reaction, i.e., by the reaction of a compound of the invention represented by the formula (1-8) with an oxidizing agent such as m-chloroperbenzoic acid or hydrogen peroxide in an inert solvent. A compound of the invention represented by the formula (1-10) can be prepared further by the reaction of the product with the above oxidizing agent.

In preparing the compound of the invention represented by the formula (1-10) from the compound of the invention represented by the formula (1-8), the compound of the invention represented by the formula (1-9) may be used as isolated or may continuously remain in the reaction mixture for further reaction.

The solvents usable for the process E are substantially the same as those for use in the process A. Examples of oxidizing agents usable are organic peroxides such as peracetic acid and various inorganic peroxides in addition to the aforementioned oxidizing agents. The oxidizing agent is used preferably in an amount of one mole or approximately one mole per mole of the compound represented by the formula (1-8) or of the compound represented by the formula (1-9).

Although not limited particularly, the reaction temperature is usually in the range of not lower than −30° C. to the boiling point of the solvent used. The reaction usually requires about 0.1 to about 24 hours for completion.

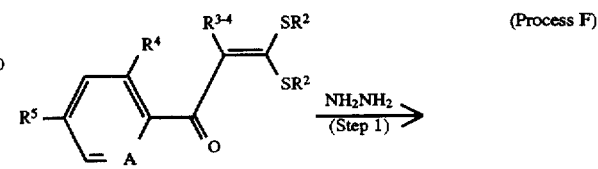

(Process F)

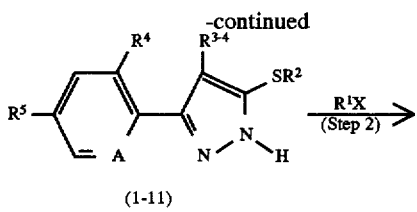

(1-11)

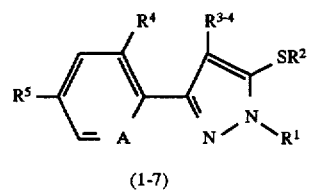

(1-7)

wherein $R^1$, $R^2$, $R^4$, $R^5$, $R^{3-4}$, A and X are the same as above.

A compound of the invention represented by the formula (1-11) can be obtained by the reaction of a ketene dithioacetal derivative represented by the formula (17) with anhydrous hydrazine or hydrazine hydrate in a suitable inert solvent in step 1 as represented above. A compound of the invention represented by the formula (1-7) can be obtained further by the reaction of the product with an alkyl halide in an inert solvent in the presence of a base in step 2.

The solvent usable, the amount of the hydrazine compound to be used, the reaction temperature and the reaction time in step 1 are substantially the same as in the process D. The solvent usable, the amount of the alkyl halide to be used, the reaction temperature and the reaction time in step 2 are substantially the same as in the process A.

The compound of the formula (1B) according to the invention can be produced also by various processes. Exemplified below is a synthetic process for preparing the compound (1B).

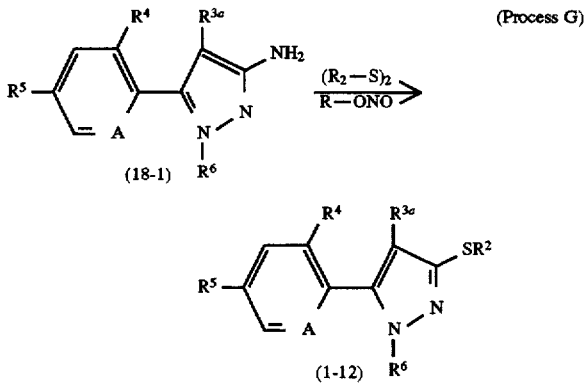

wherein $R^2$, $R^4$, $R^5$, $R^6$ and A are the same as above, $R^{3a}$ is a hydrogen atom or halogen atom, R is lower alkyl.

A compound of the invention represented by the formula (1-12) can be obtained by the above reaction, i.e., by the reaction of a pyrazole represented by the formula (18-1) with a dialkyl disulfide in the presence of an alkyl nitrite.

The pyrazole represented by the formula (18-1) can be obtained, for example, by the following reaction.

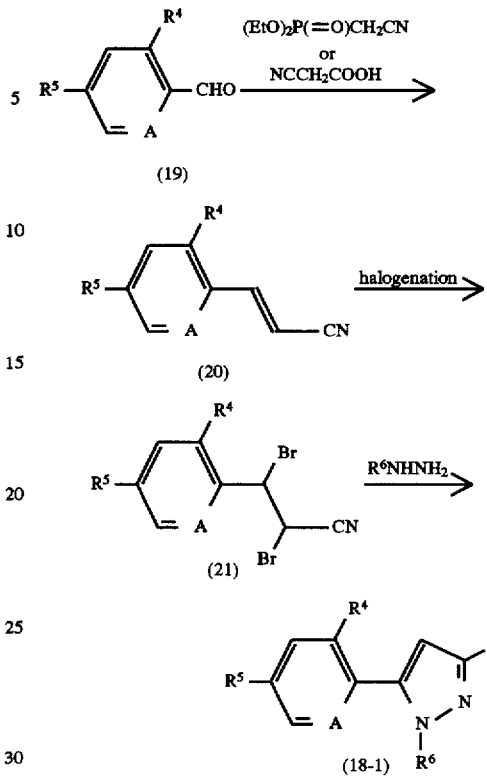

wherein $R^4$, $R^5$, $R^6$ and A are the same as above.

More specifically a compound represented by the formula (18) can be obtained by the reaction of a benzaldehyde derivative represented by the formula (19) with cianoacetic acid derivative represented by the formula $NCCH_2CO_2H$ or a phosphoric acid ester derivative such as diethyl cyanomethylphosphonate to prepare an α,β-unsaturated nitrile represented by the formula (20), reacting the nitrile with bromine to prepare a dibromonitrile compound represented by the formula (21) and subsequently reacting the compound with a hydrazine derivative.

The solvent usable, the amounts of the dialkyl disulfide and alkyl nitrite to be used, the reaction temperature and the reaction time in the process G are substantially the same as in the process C, step 2 or 5.

(Process H)

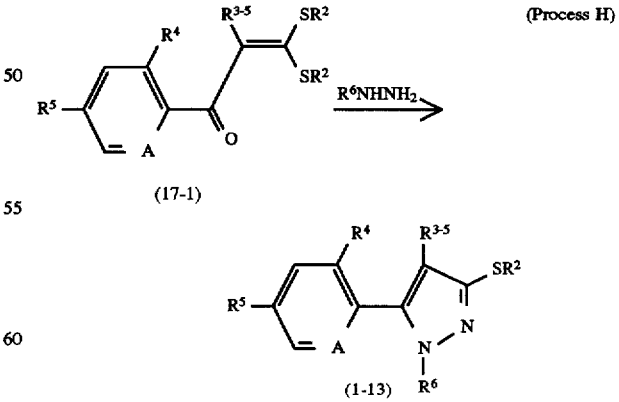

wherein $R^2$, $R^4$-$R^6$ and A are the same as above, $R^{3-5}$ is hydrogen atom or lower alkyl.

A compound of the invention represented by the formula (1-13) can be prepared by the above reaction, i.e., by the reaction of a ketene dithioacetal derivative represented by the formula (17-1) with a hydrazine derivative in a suitable inert solvent.

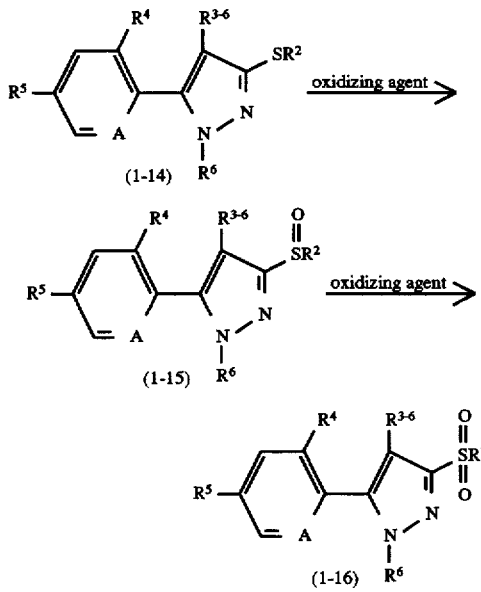

wherein $R^2$–$R^6$ and A are the same as above, $R^{3-6}$ is hydrogen atom, halogen atom or lower alkyl.

A compound of the invention represented by the formula (1-16) can be prepared by the above reaction, i.e., by the reaction of a compound of the invention represented by the formula (1-14) with an oxidizing agent in a suitable solvent to obtain a compound of the invention represented by the formula (1-15) and further by the reaction of the compound with the oxidizing agent.

In preparing the compound of the invention represented by the formula (1-16) from the compound of the invention represented by the formula (1-14), the compound of the invention represented by the formula (1-15) may be used as isolated or may continuously remain in the reaction mixture for further reaction.

The solvent usable, the oxidizing agent, the amount thereof, the reaction temperature and the reaction time in the process I are substantially the same as in the process E.

Although the compound of the invention is usable as it is as an insecticide, it is usually used in the form of an oil formulation, emulsifiable concentrate, wettable powder, suspension concentrate, granules, dusts, aerosols, fumigants or poisonous bait which is prepared usually by mixing the compound with a solid carrier, liquid carrier, gas carrier or bait or the like and as required further adding surfactants, other adjuvants for insecticidal preparations.

The compound of the invention is usable in an amount of 0.01 to 95 wt. % as contained in these formulations as their active component.

Examples of solid carriers usable for preparing the insecticidal compositions of the invention are clays including kaolin clay, diatomite, water-containing synthetic silicon oxide, bentonite, Fubasami clay and acid clay; talcs; ceramics; inorganic minerals such as Celite, quartz, sulfur, active carbon, calcium carbonate, hydrated silica; and chemical fertilizers such as ammonium sulfate, ammonium phosphate, ammonium nitrate, urea and ammonium chloride, these solid carriers being finely divided or granular. Examples of useful liquid carriers are water, alcohols such as methanol and ethanol, ketones such as acetone and methyl ethyl ketone, aromatic hydrocarbons such as benzene, toluene, xylene, ethylbenzene and methylnaphthalene, aliphatic hydrocarbons such as hexane, cyclohexane, kerosene and light oil, esters such as ethyl acetate and butyl acetate, nitriles such as acetonitrile and isobutyronitrile, ethers such as diisopropyl ether and dioxane, acid amides such as N,N-dimethylformamide and N,N-dimethylacetamide, halogenated hydrocarbons such as dichloromethane, trichloroethane and carbon tetrachloride, dimethyl sulfoxide, and vegetable oils such as soybean oil and cotton-seed oil. Examples of gas carriers, i.e., those of propellants, are butane gas, LPG (liquefied natural gas), dimethyl ether and carbon dioxide gas.

Examples of surfactants are alkylsulfuric acid esters, alkylsulfonic acid salts, alkylarylsulfonic acid salts, alkyl aryl ethers and polyoxyethylene adducts thereof, polyethylene glycol ethers, polyhydric alcohol esters and sugar alcohol derivatives.

Examples of adjuvants for the formulations, such as binders and dispersants, are casein, gelatin, polysaccharides such as starch, gum arabic, cellulose derivatives and alginic acid, lignin derivatives, bentonite, sugars and water-soluble synthetic high-molecular-weight substances such as polyvinyl alcohol, polyvinyl pyrrolidone and polyacrylic acids. Examples of stabilizers are PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants and fatty acids or esters thereof.

Examples of base materials for poisonous baits are diet components such as cereal flours, vegetable essential oils, sugars and crystalline cellulose, antioxidants such as dibutylhydroxytoluene, nordihydroguaiaretic acid, preservatives such as dehydroacetic acid, agents, such as powder of *Capsicum annuum*, for preventing erroneous ingestion and attractant flavors such as cheese flavors and onion flavors.

The formulation thus obtained can be used as it is or as diluted, for example, with water. The formulation is usable also as admixed with other insecticides, nematocides, acaricides, fungicides, herbicides, plant growth regulators, synergists, soil improver, baits, etc., or is usable simultaneously with such agents without admixing.

When to be used as an agricultural insecticide, it is desired that the compound of the invention be applied usually in an amount of 0.1 to 100 g/10 ares. When the emulsifiable concentrate, wettable powder or suspension concentrate is to be used as diluted with water, the compound is usually applied preferably at a concentration of about 10 to about 500 ppm. The granular or dust can be applied as it is without dilution. When to be used as an insecticidal composition for preventive purposes, the emulsifiable concentrate, wettable powder or suspension concentrate is usually used preferably as diluted to about 0.1 to about 500 ppm. The oil formulation, aerosol, fumigant or poisonous bait can be used as it is.

The amount or concentration of application, although exemplified above, is suitably adjustable according to the type of preparation, time, place and method of application, kind of pest insects and extent of harm suffered.

BEST MODE OF CARRYING OUT THE INVENTION

The present invention will be described below in greater detail with reference to preparation examples, formulation examples and test examples.

PREPARATION EXAMPLE 1

[Preparation of compound (3)]

Preparation of 4-bromo-3,5-dichlorobenzotrifluoride

Sodium nitrite (21.6 g) was added to 309 g of concentrated sulfuric acid at room temperature with stirring over a period of 30 minutes, followed by stirring at room temperature for 1 hour. The mixture was cooled to 10° C., 120 ml of acetic acid was added to prepare a uniform mixture, 60 ml of acetic acid solution of 69.0 g of 2,6-dichloro-4-trifluoromethylaniline was thereafter added to the mixture while holding the mixture at 10° to 15° C., and the resulting mixture was stirred at room temperature for 1 hour to obtain a solution of diazonium salt of 2,6-dichloro-4-trifluoromethylaniline.

Next, a solution of 25.2 g of sodium sulfite in 120 ml of water was added to a mixture of 99.8 g of copper sulfate pentahydrate and 61.7 g of sodium bromide in 329 ml of water at room temperature, the mixture was stirred for 15 minutes and a supernatant was removed by decantation to obtain remaining white crystals of copper bromide. The crystals were washed with water, and 156 ml of 48% aqueous hydrobromic acid solution was thereafter added thereto. To the resulting solution as cooled with ice water was added the solution of diazonium salt of 2,6-dichloro-4-trifluoromethylaniline previously prepared over a period of 1 hour, followed by stirring at 50° C. for 30 minutes. Ice water was added to the reaction mixture, and the mixture was then extracted with ethyl acetate. The resulting organic layers were combined together and washed with 5% aqueous sodium hydrogencarbonate solution and brine. The washed organic layer was dried over anhydrous magnesium sulfate and concentrated under reduced pressure, and the residue was distilled under reduced pressure, giving 71.0 g of the desired product in the form of a colorless transparent liquid (yield 80.5%). bp 65°–67° C./0.2 mmHg $^1$H-NMR (CDCl$_3$, TMS, δ ppm): 7.62(s, 2H)

PREPARATION EXAMPLE 2

[Preparation of compound (7)]

Preparation of 2,6-dichloro-4-trifluoromethylbenzaldehyde

To a mixture of 65.2 ml of n-butyllithium (1.61M in hexane) and 100 ml of anhydrous ether was added dropwise 29.3 g of 4-bromo-3,5-dichlorobenzotrifluoride (3) in 20 ml of anhydrous ether at −78° C. over a period of 15 minutes, followed by stirring for 20 minutes. Next, 100 ml an anhydrous ether solution of 21.8 ml of N,N-dimethylformamide was added dropwise to the mixture at the same temperature, followed by stirring at −78° C. for 30 minutes and then at 0° C. for 30 minutes. To the reaction mixture was thereafter added 400 ml of aqueous 1N phosphoric acid. The resulting mixture was further stirred for 30 minutes.

The reaction mixture was extracted with ether, and the ethereal layers were combined together, washed with brine, dried over anhydrous magnesium sulfate and concentrated under reduced pressure. The residue obtained was distilled under reduced pressure, giving 26.7 g of the desired compound in the form of a colorless oil (yield 78.3%).

bp 114°–115° C./19 mmHg $^1$H-NMR (CDCl$_3$, TMS, δ ppm): 7.65(s, 2H), 10.47(s, 1H)

PREPARATION EXAMPLE 3

[Preparation of compound (11)]

Preparation of 2,6-dichloro-4-trifluoromethylbenzoic acid

To a mixture of 65.2 ml of n-butyllithium (1.61M in hexane) and 100 ml of anhydrous ether was added dropwise 29.3 g of 4-bromo-3,5-dichlorobenzotrifluoride (3) in 30 ml of anhydrous ether at −78° C., followed by stirring for 20 minutes. Subsequently, 10 g of dry ice crashed into small pieces was added in small portions to the reaction mixture, followed by stirring at room temperature for 1.5 hours. Ice water was added to the reaction mixture, the mixture was thereafter extracted with ether, and the combined extract was subjected to reverse extraction with 10% aqueous sodium carbonate solution. The aqueous layer was acidified with 6N hydrochloric acid, followed by extraction with ethyl acetate, washing with brine and drying over anhydrous magnesium sulfate. Removal of the solvent under reduced pressure gave 20.4 g of the desired product in the form of white crystals (crude yield 79.1%). mp 117°~118° C.

$^1$H-NMR (CDCl$_3$, TMS, δ ppm): 6.21(br, s, 1H), 7.64(s, 2H)

PREPARATION EXAMPLE 4

[Preparation of compound (4)]

Preparation of ethyl 2,6-dichloro-4-trifluoromethylbenzoate

To a mixture of 65.2 ml of n-butyllithium (1.61M in hexane) and 100 ml of anhydrous ether was added dropwise 29.3 g of 4-bromo-3,5-dichlorobenzo-trifluoride (3) in 30 ml of anhydrous ether at −78° C., followed by stirring for 20 minutes. Subsequently, 13.3 ml of diethyl carbonate in 50 ml of anhydrous ether was added dropwise to the mixture, followed by stirring at −78° C. for 30 minutes and then at 0° C. for 30 minutes. Ice water was added to the reaction mixture, the mixture was extracted with ether, and the combined ethereal layer was washed with brine, dried over anhydrous magnesium sulfate and concentrated under reduced pressure. The resulting residue was distilled under reduced pressure, giving 18.3 g of the desired product in the form of a colorless oil (yield 63.8%).

bp 62°–67° C./0.3 mmHg $^1$H-NMR (CDCl$_3$, TMS, δ ppm): 1.42(t, 3H), 4.49(q, 2H), 7.61(s, 2H)

PREPARATION EXAMPLE 5

[Preparation of compound (9)]

Preparation of 3,5-dichloro-4-(1-hydroxyethyl) benzotrifluoride

To a mixture of 65.2 ml of n-butyllithium (1.61M in hexane) and 100 ml of anhydrous ether was added dropwise 29.3 g of 4-bromo-3,5-dichlorobenzotrifluoride (3) in 30 ml of anhydrous ether at −78° C., followed by stirring for 20 minutes. Subsequently, 6.2 ml of acetaldehyde in 50 ml of anhydrous ether was added dropwise to the mixture at the same temperature, followed by stirring at 0° C. Ice waster was added to the reaction mixture, followed by extraction with ether, drying over anhydrous magnesium sulfate and concentration under reduced pressure to give 23.5 g of the desired product in the form of a colorless oil (crude yield 90.7% ).

$^1$H-NMR (CDCl$_3$, TMS, δ ppm): 1.42 (d, 2H), 2.62(s, 3H), 5.25(q, 1H), 7.61(s, 2H)

PREPARATION EXAMPLE 6

[Preparation of compound (10)]
Preparation of 4-acetyl-3,5-dichlorobenzotrifluoride An anhydrous methylene chloride solution (50 ml) of 23.5 g of 3,5-dichloro-4-(1-hydroxyethyl)benzotrifluoride (9) was added at a time to 100 ml of an anhydrous methylene chloride suspension of 30.0 g of pyridinium chlorochromate and 20 g of Celite at room temperature, and the mixture was stirred overnight. The reaction mixture was diluted with 100 ml of ether and thereafter applied to a column packed with 100 g of silica gel. Ether was used for elution, and the eluent was concentrated under reduced pressure to obtain 18.7 g of the desired compound in the form of a yellow oil (crude yield 72.8%).

$^1$H-NMR (CDCl$_3$, TMS, δ ppm): 1.17(t, 3H), 2.77(q, 2H), 2.58(s, 3H), 7.60 (s, 2H)

PREPARATION EXAMPLE 7

[Preparation of compound (8)]
Preparation of ethyl 3-(2,6-dichloro-4-trifluoromethylphenyl)-3-hydroxypropionate Ethyl bromoacetate (13.7 ml) was added to a suspension of 30.0 g of 2,6-dichloro-4-trifluoromethylbenzaldehyde (7), 50 ml of trimethoxyborane and 8.5 g of zinc powder in 50 ml of anhydrous tetrahydrofuran with vigorous stirring at room temperature, and the mixture was stirred overnight. The reaction mixture was poured into a mixture of 100 ml of 10% hydrochloric acid and 10 ml of acetic acid, and the resulting mixture was filtered through Celite. The aqueous filtrate was neutralized with a 5% aqueous solution of sodium hydrogencarbonate, followed by extraction with ethyl acetate, drying over anhydrous magnesium sulfate and concentration under reduced pressure, affording 40.7 g of the desired compound in the form of a pale green oil (quantitative crude yield).

$^1$H-NMR (CDCl$_3$, TMS, δ ppm): 1.26(t, 3H), 2.75(dd, 1H), 3.25(dd, 2H), 4.25(q, 2H), 5.95(m, 1H), 7.57(s, 2H)

PREPARATION EXAMPLE 8

[Preparation of compound (5)]
Preparation of ethyl 3-(2,6-dichloro-4-trifluoromethylphenyl)-3-oxopropionate An anhydrous methylene chloride solution of 20.0 g of ethyl 3-(2,6-dichloro-4-trifluoromethylphenyl)-3-hydroxypropionate (8) was added to a suspension of 19.6 g of pyridinium chlorochromate and 15 g of Celite in 100 ml of methylene chloride at room temperature, and the mixture was stirred overnight. The reaction mixture was diluted with 200 ml of ether and thereafter applied to a column packed with 100 g of silica gel. Ether was used for elution, and the eluent was concentrated under reduced pressure, giving 8.3 g of the desired compound in the form of a pale brown oil (yield 41.91%).

$^1$H-NMR (CDCl$_3$, TMS, δ ppm): 1.38(t, 3H), 3.95(s, 1H), 4.20(q, 2H), 7.70 (s, 2H), 12.10 (s, 1H)

PREPARATION EXAMPLE 9

[Preparation of compound (8)]
Preparation of ethyl 3-(2,6-dichloro-4-trifluoromethylphenyl)-3-hydroxy-2-methylpropionate To 3.8 ml of anhydrous diisopropylamine in 50 ml anhydrous tetrahydrofuran was added 14.7 ml of n-butyllithium (1.61 moles/liter in hexane) at 0° C., the mixture was stirred at 0° C. for 30 minutes, and 2.4 ml of ethyl propionate in 10 ml of anhydrous tetrahydrofuran was thereafter added to the mixture. The resulting mixture was stirred at −78° C. for 1 hour, and 5.0 g of 2,6-dichloro-4-trifluoromethylbenzaldehyde (7) in 10 ml of anhydrous tetrahydrofuran was thereafter added to the mixture, followed by stirring at −78° C. for 30 minutes and then at room temperature for 1 hour. The reaction mixture was poured into ice water, followed by extraction with ethyl acetate, washing with brine, drying over anhydrous magnesium sulfate and concentration under reduced pressure. The residue was purified by column chromatography on silica gel (eluent: ethyl acetate/hexane=1/6), affording 7.2 g of the desired product in the form of a yellow oil (yield 91.1%).

$^1$H-NMR (CDCl$_3$, TMS, δ ppm): 0.95–1.40(m, 3H), 1.42(d, 3H), 3.50(m, 1H), 3.81–4.40(m, 2H), 5.80(dd, 1H), 7.60(s, 2H)

PREPARATION EXAMPLE 10

[Preparation of compound (12)]
Preparation of 2,6-dichloro-4-trifluoromethylbenzoyl chloride A mixture of 20.4 g of 2,6-dichloro-4-trifluoromethylbenzoic acid (11), 18.8 g of thionyl chloride and a small amount of anhydrous N,N-dimethylformamide was stirred at 90° C. overnight. The thionyl chloride was distilled off, and the resulting residue was distilled under reduced pressure to obtain 21.7 g of the desired compound in the form of a colorless liquid (quantitative yield).

$^1$H-NMR (CDCl$_3$, TMS, δ ppm): 7.66(s, 2H)

PREPARATION EXAMPLE 11

[Preparation of compound (6)]
Preparation of 3-(2,6-dichloro-4-trifluoromethylphenyl)-5-hydroxy-1-methylpyrazole A solution of 1.0 g of methylhydrazine in 15 ml of ethanol was added dropwise to 6.0 g of ethyl 3-(2,6-dichloro-4-trifluoromethylphenyl)-3-oxopropionate (5) in 50 ml of ethanol at room temperature, and the mixture was thereafter stirred at room temperature for 1 hour and further refluxed overnight. The reaction mixture was concentrated under reduced pressure to obtain a residue, which was washed with hexane to give 2.8 g of the desired compound in the form of white crystals (crude yield 50.0%).

$^1$H-NMR (CD$_3$OD, δ ppm): 3.28(s, 3H), 6.18(s, 1H), 7.60(s, 1H)

PREPARATION EXAMPLE 12

[Preparation of compound (2)]
Preparation of 3-(2,6-dichloro-4-trifluoromethylphenyl)-5-mercapto-1-methylpyrazole A suspension of 1.0 g of 3-(2,6-dichloro-4-trifluoromethylphenyl)-5-hydroxy-1-methylpyrazole (6) and 0.7 g of Lawesson's reagent in 10 ml of toluene were refluxed with stirring for 3 hours. The solvent was distilled off under reduced pressure, and the resulting residue was purified by column chromatography on silica gel (eluent: ethyl acetate/hexane=1/6), giving 0.3 g of the desired compound in the form of colorless crystals (yield 27.3%).

$^1$H-NMR (CDCl$_3$, TMS, δ ppm): 3.90(s, 3H), 6.51(s, 1H), 7.62(s, 2H)

PREPARATION EXAMPLE 13

[Preparation of compound (1-1)]
Preparation of 3-(2,6-dichloro-4-trifluoromethylphenyl)-1-methyl-5-methylsulfenylpyrazole (compound 1)

A suspension of 0.5 g of 3-(2,6-dichloro-4-trifluoromethylphenyl)-5-mercapto-1-methylpyrazole (2), 2.3 g of methyl iodide and 0.4 g of anhydrous potassium carbonate in 10 ml of acetonitrile was refluxed overnight with stirring. The reaction mixture was cooled to room temperature and filtered through Celite, and the filtrate was concentrated under reduced pressure. The residue was purified by chromatography on silica gel to obtain 0.51 g of the desired product in the form of white crystals.

PREPARATION EXAMPLE 14

[Preparation of compound (1-1)]
Preparation of 3-(2,6-dichloro-4-trifluoromethylphenyl)-1-methyl-5-(trifluoromethylsulfenyl)pyrazole (compound 5)

To a suspension of 0.13 g of 60% oily sodium hydride in 10 ml of anhydrous tetrahydrofuran was added dropwise 0.7 g of 3-(2,6-dichloro-4-trifluoromethylphenyl)-1-methyl-5-mercaptopyrazole (2) in 2.0 ml of anhydrous tetrahydrofuran at 0° C., and the mixture was stirred at room temperature for 1 hour. Subsequently, with addition of an excess of trifluoromethyl iodide, the mixture was stirred for 4 hours as contained in a sealed container. Ice water was added to the reaction mixture, the mixture was thereafter extracted with ethyl acetate, and the extracts were combined together, washed with brine and dried over magnesium sulfate. The solvent was distilled off under reduced pressure to obtain a residue, which was then purified by column chromatography on silica gel (eluent: ethyl acetate/hexane=1/5), giving 0.6 g of the desired compound in the form of a colorless oil (yield 48.6%).

PREPARATION EXAMPLE 15

[Preparation of compound (1-9)]
Preparation of 3-(2,6-dichloro-4-trifluoromethylphenyl)-1-methyl-5-methylsulfinylpyrazole (compound 6)

A 0.3 g quantity of 70% m-chloroperbenzoic acid was slowly added to 0.3 g of 3-(2,6-dichloro-4-trifluoromethylphenyl)-1-methyl-5-methylsulfenylpyrazole (compound 1) in 20 ml of anhydrous chloroform at room temperature with stirring, followed by stirring for 3 hours. The reaction mixture was poured into a saturated aqueous solution of sodium hydrogencarbonate, an organic layer was then separated off, washed with 5% aqueous sodium hydroxide solution and with brine and dried over anhydrous magnesium sulfate. The solvent was thereafter distilled off under reduced pressure, giving 0.3 g of the desired compound in the form of white crystals (quantitative crude yield).

PREPARATION EXAMPLE 16

[Preparation of compound (1-10)]
Preparation of 3-(2,6-dichloro-4-trifluoromethylphenyl)-1-methyl-5-methylsulfonylpyrazole (compound 7)

A 0.3 g quantity of 70% m-chloroperbenzoic acid was slowly added to 0.2 g of 3-(2,6-dichloro-4-trifluoromethylphenyl)-1-methyl-5-methylsulfenylpyrazole (compound 6) in 20 ml of anhydrous chloroform at room temperature with stirring, followed by further stirring overnight. The reaction mixture was poured into a 10% aqueous sodium sulfite solution, an organic layer was then separated off, washed with 5% aqueous sodium hydroxide solution and with brine and dried over anhydrous magnesium sulfate. The solvent was thereafter distilled off under reduced pressure, giving 0.3 g of the desired compound in the form of white crystals (quantitative crude yield).

PREPARATION EXAMPLE 17

[Preparation of compound (1-3)]
Preparation of 4-chloro-3-(2,6-dichloro-4-trifluoromethylphenyl)-1-methyl-5-methylsulfenylpyrazole (compound 8)

A 0.3 g quantity of sulfuryl chloride was added to 1.2 g of 3-(2,6-dichloro-4-trifluoromethylphenyl)-1-methyl-5-methylsulfenylpyrazole (compound 1) in 5 ml of anhydrous carbon tetrachloride at room temperature, followed by stirring at room temperature for 2 hours. The reaction mixture was poured into cold water, and the resulting mixture was extracted with methylene chloride. The organic layer was washed with 10% aqueous sodium hydrogen carbonate solution and with brine, and dried over anhydrous magnesium sulfate. The solvent was distilled off under reduced pressure to obtain a residue, which was then purified by column chromatography on silica gel (eluent: ether/hexane= 1/5), giving 1.0 g of the desired compound in the form of white crystals (yield 83.3%).

PREPARATION EXAMPLE 18

[Preparation of compound (16)]
Preparation of 3-(2,6-dichloro-4-trifluoromethylphenyl)-3-oxopropionitrile A solution of 4.1 ml of acetonitrile anhydrous in 50 ml of tetrahydrofuran was added dropwise to a mixture of 49.1 ml of 1.67M n-butylhexane and 100 ml of anhydrous tetrahydrofuran at −78° C., and the mixture was stirred for 1 hour. To the mixture was added dropwise 22.5 g of ethyl 2,6-dichloro-4-trifluoromethylbenzoate in 20 ml of anhydrous tetrahydrofuran over a period of 10 minutes, and the mixture was further stirred for 10 minutes. Water was then added to the mixture. The resulting mixture was extracted with ethyl acetate, and the extracts were combined together, washed with brine and dried over anhydrous magnesium sulfate. The solvent was distilled off under reduced pressure, and the residue was purified by recrystallization, giving 18.7 g of the desired compound in the form of brown crystals (yield 84.6%), m.p. 119°–121° C.

$^1$H-NMR (CDCl$_3$, TMS, δ ppm): 3.95(s, 2H), 7.70(s, 2H).

PREPARATION EXAMPLE 19

[Preparation of compound (17) and compound (1-7)]
Preparation of 3-(2,6-dichloro-4-trifluoromethylphenyl)-4-cyano-1-methyl-5-methylsulfenylpyrazole (compound 12)

A 1.93 g quantity of 60% oily sodium hydride was added in small portions to a solution of 4.8 g of 3-(2,6-dichloro-4-trifluoromethylphenyl)-3-oxopropionitrile (16) and 1.3 g of carbon disulfide in 50 ml of anhydrous N,N-dimethylformamide at 0° C., and the mixture was stirred for 1 hour. Subsequently, 2.2 ml of methyl iodide was added dropwise to the mixture over a period of 10 minutes, followed by stirring for 1 hour.

Ice water was added to the reaction mixture, followed by extraction with ethyl acetate, washing with brine, drying over anhydrous magnesium sulfate and removal of the solvent under reduced pressure to obtain 5.3 g of a brown residue. To 100 ml of an ethanol solution of the crude product was added dropwise a solution of 0.94 g of methylhydrazine in 10 ml of ethanol at room temperature, and the mixture was stirred for 1 hour and then refluxed for 2 hours. The reaction mixture was concentrated under reduced pressure to obtain a residue, which was then dissolved in ethyl acetate. The solution was washed with 1N hydrochloric acid and brine and dried over anhydrous magnesium sulfate. The solvent was distilled off under reduced pressure, and the resulting residue was purified by column chromatography on silica gel (eluent: ether/hexane=1/7), giving 0.3 g of the desired compound in the form of colorless crystals (yield 5.0%).

PREPARATION EXAMPLE 20

[Preparation of compound (13)]

Preparation of 5-amino-3-(2,6-dichloro-4-trifluoromethylphenyl)-1-methylpyrazole A solution of 0.3 g of methylhydrazine in 5 ml of ethanol was added dropwise to a solution of 1.4 g of 3-(2,6-dichloro-4-trifluoromethylphenyl)-3-oxopropionitrile (16) in 30 ml of ethanol at room temperature, and the mixture was stirred for 30 minutes and thereafter refluxed overnight. Ice water was added to the reaction mixture, the resulting mixture was extracted with ethyl acetate, and the extracts were combined together and subjected to reverse extraction with 10% hydrochloric acid. The 10% hydrochloric acid layer was made weakly alkaline with a saturated sodium carbonate aqueous solution and thereafter extracted with ethyl acetate, followed by washing with brine and drying over anhydrous magnesium sulfate. Removal of the solvent under reduced pressure gave a residue, which was purified by column chromatography on silica gel (eluent: ethyl acetate/hexane= 2/3), affording 1.0 g of the desired compound in the form of light yellow crystals (yield 59.8%).

mp 161°–163° C.

$^1$H-NMR (CDCl$_3$, TMS, δ ppm): 3.40(br, s, 2H), 3.75(s, 3H), 5.65(s, 1H), 7.60(s, 2H)

PREPARATION EXAMPLE 21

[Preparation of compound (14)]

Preparation of 5-amino-3-(2,6-dichloro-4-trifluoromethylphenyl)-1-methyl-4-nitropyrazole To 2.8 g of concentrated nitric acid was added dropwise 3.7 g of concentrated sulfuric acid at room temperature, followed by stirring for 10 minutes to obtain a mixed acid solution. A 0.5 g quantity of 5-amino-3-(2,6-dichloro-4-trifluoromethylphenyl)-1-methylpyrazole (13) was added in small portions to the solution at 60° C., and the mixture was stirred at the same temperature for 1 hour. The reaction mixture was added to water, the resulting mixture was extracted with ether, and the aqueous layer was made weakly alkaline with a saturated sodium carbonate aqueous solution and then extracted with ethyl acetate, followed by washing with brine and drying over anhydrous magnesium sulfate. Removal of the solvent gave 0.2 g of the desired compound in the form of orange crystals (yield 35.1%), m.p. 107°–108° C.

$^1$H-NMR (CDCl$_3$, TMS, δ ppm): 3.0(br, s, 2H), 4.05(s, 3H), 7.71(s, 2H)

PREPARATION EXAMPLE 22

[Preparation of compound (1-4)]

Preparation of 3-(2,6-dichloro-4-trifluoromethylphenyl)-1-methyl-5-methylsulfenyl-4-nitropyrazole (compound 13)

First 1.4 g of dimethyl disulfide and then 0.96 g of tert-butyl nitrite were added at 0° C. to a solution of 1.1 g of 5-amino-3-(2,6-dichloro-4-trifluoromethylphenyl)-1-methyl-4-nitropyrazole (14) in 25 ml of anhydrous methylene chloride, and the mixture was stirred at room temperature overnight. The reaction mixture was concentrated under reduced pressure, the resulting residue was purified by column chromatography on silica gel (eluent: hexane/ethyl acetate=3/1) to afford 0.6 g of the desired compound in the form of a yellow consistent liquid (yield 60.1%).

PREPARATION EXAMPLE 23

[Preparation of compound (1-5)]

Preparation of 4-amino-3-(2,6-dichloro-4-trifluoromethylphenyl)-1-methyl-5-(methylsulfenyl)pyrazole (compound 14)

A suspension of 0.15 g of 3-(2,6-dichloro-4-trifluoromethylphenyl)-1-methyl-5-methylsulfenyl-4-nitropyrazole (compound 13) and 0.1 g of 10% palladium carbon in ethanol was stirred for 1 hour while introducing hydrogen gas into the mixture at room temperature at atmospheric pressure. The reaction mixture was filtered through Celite, the filtrate was concentrated under reduced pressure, and the resulting residue was purified by column chromatography on silica gel (eluent: ether/hexane=1/4) to obtain 0.6 g of the desired compound in the form of a consistent liquid (yield 67.3%).

PREPARATION EXAMPLE 24

[Preparation of compound (1-7)]

Preparation of 3-(2,6-dichloro-4-trifluoromethylphenyl)-5-methylsulfenyl-1-phenylpyrazole (compound 17)

Phenylhydrazine (0.11 ml) was added to a solution of 0.8 g of 3,3-bis[methylthio]-1-(2,6-dichloro-4-trifluoromethylphenyl)-2-propen-1-one in 10 ml of ethanol at room temperature, and the mixture was refluxed for 1 hour. The solvent was distilled of under reduced pressure to obtain a residue, which was purified by column chromatography on silica gel (eluent: ether/hexane=1/6), giving 0.17 g of the desired compound in the form of a pale brown oil (yield 43.6%).

PREPARATION EXAMPLE 25

[Preparation of compound (15)]

Preparation of 5-amino-3-(2,6-dichloro-4-trifluoromethylphenyl)-1-methyl-4-(trifluoromethylsulfenyl)pyrazole A solution of 2 ml of trifluoromethylsulfenyl chloride in 5 ml of anhydrous methylene chloride was added to a solution of 0.3 g of 5-amino-3-(2,6-dichloro-4-trifluoromethylphenyl)-1-methylpyrazole (13) in 40 ml of anhydrous methylene chloride at −78° C., and the mixture was stirred at room temperature overnight. The reaction mixture was concentrated under reduced pressure to obtain a residue, which was purified by column chromatography on silica gel (eluent: ethyl acetate/hexane=1/1) to obtain 0.3 g of the desired compound in the form of pale yellow crystals (yield 75.0%).

mp 177°–179° C.

$^1$H-NMR (CDCl$_3$, TMS, δ ppm): 3.79(s, 3H), 4.17(br, s, 2H), 7.65(s, 2H)

PREPARATION EXAMPLE 26

[Preparation of compound (1-11)]

Preparation of 3-(2,6-dichloro-4-trifluoromethylphenyl)-5-methylsulfenylpyrazole (compound 16)

Hydrazine monohydrate (0.51 ml) was added dropwise to a solution of 3.6 g of 3,3-bis[methylthio]-1-(2,6-dichloro-4-trifluoromethylphenyl)-2-propen-1-one (17) in 40 ml of ethanol at room temperature, and the mixture was stirred for 45 minutes and then refluxed for 4 hours. The reaction mixture was concentrated under reduced pressure to obtain a residue, which was purified by column chromatography on silica gel (eluent: ether/hexane=2/5) to afford 3.3 g of the desired compound in the form of white crystals.

PREPARATION EXAMPLE 27

[Preparation of compound (1-7)]

Preparation of 1-butyl-3-(2,6-dichloro-4-trifluoromethylphenyl)-5-(methylsulfenyl)pyrazole (compound 21)

A solution of 0.8 g of 3-(2,6-dichloro-4-trifluoromethylphenyl)-5-(methylsulfenyl)pyrazole (compound 16), 0.7 g of anhydrous potassium carbonate and 0.4 g of n-butyl bromide in 25 ml of acetone were refluxed for 4 hours. The reaction mixture was filtered through Celite, the filtrate was concentrated under reduced pressure and the resulting residue was purified by column chromatography on silica gel (eluent: ether/hexane=1/20) to obtain 0.3 g of the desired product in the form of a light brown oil (yield 69.6%).

PREPARATION EXAMPLE 28

[Preparation of compound (1-7)]

Preparation of 3-(2,6-dichloro-4-trifluoromethylphenyl)-5-methylsulfenyl-1-(trifluoromethyl)pyrazole (compound 24)

Sodium hydride was added dropwise to a suspension of 0.5 g of 3-(2,6-dichloro-4-trifluoromethylphenyl)-5-(methylsulfenyl)pyrazole (compound 16) in 5 ml of anhydrous N,N-dimethylformamide at 0° C., and the mixture was stirred at room temperature. An excess of trifluoromethyl iodide was introduced into the reaction mixture, and the resulting mixture was stirred for 3 hours with the reactor closed. The reaction mixture was poured into water, followed by extraction with ether, washing with brine and drying over anhydrous magnesium sulfate. The solvent was distilled off under reduced pressure to obtain a residue, which was purified by column chromatography on silica gel (eluent: chloroform/hexane=1/20), giving 0.2 g of the desired product in the form of light brown oil (yield 33.3%).

Tables 1 and 2 show the compounds prepared in the same manner as in the foregoing preparation examples. In the tables, n-Pr stands for n-$C_3H_7$, and n-Bu for n-$C_4H_9$.

TABLE 1

(1)

$F_3C$— ...phenyl-pyrazole structure with substituents Cl, $R^3$, $S(O)nR^2$, A, N, N, $R^1$

| Compound | $R^1$ | $R^2$ | $R^3$ | A | n | Process | m.p. (°C.) |
|---|---|---|---|---|---|---|---|
| 1 | $CH_3$ | $CH_3$ | H | C—Cl | 0 | A,D | 45–46 |
| 2 | $CH_3$ | n-Pr | H | C—Cl | 0 | A | Oil |
| 3 | $CH_3$ | Benzyl | H | C—Cl | 0 | A | Oil |
| 4 | $CH_3$ | Propargyl | H | C—Cl | 0 | A | 52–53 |
| 5 | $CH_3$ | $CF_3$ | H | C—Cl | 0 | A | Oil |
| 6 | $CH_3$ | $CH_3$ | H | C—Cl | 1 | E | 128–130 |
| 7 | $CH_3$ | $CH_3$ | H | C—Cl | 2 | E | 105–106 |
| 8 | $CH_3$ | $CH_3$ | Cl | C—Cl | 0 | B | 77–79 |
| 9 | $CH_3$ | $CH_3$ | Cl | C—Cl | 1 | E | 101–103 |
| 10 | $CH_3$ | $CH_3$ | Br | C—Cl | 0 | B | 87–88 |
| 11 | $CH_3$ | $CH_3$ | $CH_3$ | C—Cl | 0 | A | 55–56 |
| 12 | $CH_3$ | $CH_3$ | CN | C—Cl | 0 | D | 102–103 |
| 13 | $CH_3$ | $CH_3$ | $NO_2$ | C—Cl | 0 | C | 123–125 |
| 14 | $CH_3$ | $CH_3$ | $NH_2$ | C—Cl | 0 | C | viscous liquid |
| 15 | $CH_3$ | $CH_3$ | Phenyl | C—Cl | 0 | A | viscous liquid |
| 16 | H | $CH_3$ | H | C—Cl | 0 | F | 118–119 |
| 17 | Phenyl | $CH_3$ | H | C—Cl | 0 | D | Oil |
| 18 | $CH_3$ | $CH_3$ | $SCF_3$ | C—Cl | 0 | C | Oil |
| 19 | $CH_3$ | $CF_3$ | Cl | C—Cl | 0 | A | viscous liquid |

TABLE 2

| Compound | $R^1$ | $R^2$ | $R^3$ | A | n | Process | m.p. (°C.) |
|---|---|---|---|---|---|---|---|
| 20 | $C_2H_5$ | $CH_3$ | H | C—Cl | 0 | F | Oil |
| 21 | n-Bu | $CH_3$ | H | C—Cl | 0 | F | Oil |
| 22 | Benzyl | $CH_3$ | H | C—Cl | 0 | F | Oil |
| 23 | $CH_2F$ | $CH_3$ | H | C—Cl | 0 | F | Oil |
| 24 | $CF_3$ | $CH_3$ | H | C—Cl | 0 | F | Oil |
| 25 | $C_2H_5$ | $CH_3$ | H | C—Cl | 1 | E | viscous liquid |
| 26 | $CH_3$ | n-Pr | H | C—Cl | 2 | E | 101–103 |
| 27 | $CH_3$ | $CH_3$ | $SCH_3$ | C—Cl | 0 | C | viscous liquid |
| 28 | $CH_3$ | $CH_3$ | F | C—Cl | 0 | B | viscous liquid |
| 29 | $CH_3$ | Allyl | H | C—Cl | 0 | A | viscous liquid |
| 30 | $CH_3$ | $CH_3$ | H | CH | 0 | A | viscous liquid |
| 31 | $CH_3$ | $CH_3$ | H | N | 0 | D | viscous liquid |

Analytical data of $^1$H-NMR($CDCl_3$, TMS, δ ppm) of Compounds 1~31 are shown below.

(Compound 1) 2.48(s, 3H), 3.96(s, 3H), 6.34(s, 9H), 7.64(s, 2H)

(Compound 2) 1.03(t, 3H), 1.60(q, 2H), 2.80(t, 2H), 3.99(s, 3H), 6.42(s, 1H), 7.64(s, 2H)

(Compound 3) 3.55(s, 3H), 3.91(s, 2H), 6.37(s, 1H), 7.25(m, 5H), 7.64(s, 2H)

(Compound 4) 2.28(t, 1H), 3.52(d, 2H), 4.06(s, 3H), 6.60(s, 1H), 7.65(s, 2H)

(Compound 5) 4.01(s, 3H), 6.50(s, 2H), 7.61(s, 2H)

(Compound 6) 3.05(s, 3H), 4.20(s, 3H), 6.75(s, 1H), 7.65(s, 2H)

(Compound 7) 3.27(s, 3H), 4.29(s, 3H), 7.00(s, 1H), 7.70(s, 2H)

(Compound 8) 2.43(s, 3H), 4.04(s, 3H), 7.67(s, 2H)

(Compound 9) 3.35(s, 3H), 4.30(s, 3H), 7.78(s, 2H)

(Compound 10) 2.43(s, 3H), 4.09(s, 3H), 7.66(s, 2H)

(Compound 11) 1.89(s, 3H), 2.23(s, 3H), 3.94(s, 3H), 7.57(s, 2H)

(Compound 12) 1.99(s, 3H), 3.34(s, 3H), 7.69(s, 2H)

(Compound 13) 2.63(s, 3H), 4.10(s, 3H), 7.68(s, 2H)

(Compound 14) 2.29(s, 3H), 3.91(s, 3H), 7.66(s, 2H)

(Compound 15) 2.22(s, 3H), 4.11(s, 3H), 7.26(s, 5H), 7.56(s, 2H)

(Compound 16) 2.53(s, 3H), 6.41(s, 1H), 7.65(s, 2H), 10.5(br, s, 1H)

(Compound 17) 2.44(s, 3H), 6.45(s, 1H), 7.4–7.9(m, 7H)

(Compound 18) 2.48(s, 3H), 4.13(s, 3H), 7.67(s, 2H)

(Compound 19) 4.01(s, 3H), 7.60(s, 2H)

(Compound 20) 1.48(t, 3H), 2.54(s, 3H), 4.30(q, 2H), 6.33(s, 1H), 7.64(s, 2H)

(Compound 21) 0.95–2.05(m, 7H), 2.50(s, 3H), 4.25(t, 2H), 6.32(s, 1H), 7.64(s, 2H)

(Compound 22) 2.30(s, 3H), 5.50(s, 2H), 6.42(s, 1H), 7.29(m, 5H), 7.65(s, 2H)

(Compound 23) 2.52(s, 3H), 5.90(s, 1H), 6.50(s, 2H), 7.65(s, 2H)

(Compound 24) 2.48(s, 3H), 6.38(s, 1H), 7.61(s, 2H)

(Compound 25) 1.55(t, 3H), 3.00(s, 3H), 4.50(q, 2H), 6.99(s, 1H), 7.62(s, 2H)

(Compound 26) 1.08(t, 3H), 1.85(q, 2H), 3.23(m, 2H), 4.29(s, 3H), 6.94(s, 1H), 7.67(s, 2H)

(Compound 27) 2.20(s, 3H), 2.40(s, 3H), 3.95(s, 3H), 7.65(s, 2H)

(Compound 28) 2.43(s, 3H), 4.00(s, 3H), 7.66(s, 2H)

(Compound 29) 2.43(s, 3H), 3.41(dd, 2H), 5.06(m, 1H), 5.5–6.25(m, 2H), 4.05(s, 3H), 6.62(s, 1H), 7.65(s, 2H)

(Compound 30) 2.46(s, 3H), 3.96(s, 3H), 6.88(s, 1H), 7.54(d, 1H), 7.69(s, 1H), 7.96(d, 1H)

(Compound 31) 2.47(s, 3H), 4.02(s, 3H), 7.07(s, 1H), 8.01(d, 1H), 8.43(m, 1H)

PREPARATION EXAMPLE 29

[Preparation of compound (20)]
Preparation of 2,6-dichloro-4-trifluoromethyl cinnamic nitrile Piperidine (0.99 ml) and 9.2 g of cyanoacetic acid were added dropwise to a solution of 24.3 g of 2,6-dichloro-4-trifluoromethylbenzaldehyde (19) in 70 ml of pyridine, and the mixture was stirred at room temperature for 1 hour and further refluxed for 14 hours. The solvent was distilled off under reduced pressure to obtain a residue, which was then dissolved in ethyl acetate. The organic layer was washed with 1N hydrochloric acid, then with water and thereafter with brine, dried over anhydrous magnesium sulfate and concentrated under reduced pressure. The resulting residue was purified by column chromatography on silica gel, giving 17.3 g of the desired compound in the form of a white solid (yield 65.0%).

$^1$H-NMR(CDCl$_3$, TMS, δ ppm): 6.17(d, 1H), 7.42(s, 2H), 7.48(d, 1H)

PREPARATION EXAMPLE 30

[Preparation of compound (21)]
Preparation of 3-(2,6-dichloro-4-trifluoromethyl)phenyl-1,2-dibromopropionitrile Bromine (3.4 ml) was added dropwise to a solution of 17.3 g of 2,6-dichloro-4-trifluoromethyl cinnamic nitrile (20) in 70 ml of acetic acid, followed by stirring at 60° C. for 3 hours. The mixture was cooled to room temperature, the solvent was distilled off under reduced pressure, the residue obtained was dissolved in methylene chloride, and the organic layer was washed with a 10% aqueous sodium thiosulfate solution and 10% sodium hydrogencarbonate brine. The layer was dried over anhydrous magnesium sulfate and concentrated under reduced pressure, giving 24.6 g of the desired compound in the form of a brown oil (yield 89.1%).

$^1$H-NMR(CDCl$_3$, TMS, δ ppm): 6.76(d, 1H), 7.62(s, 2H), 8.15(d, 1H)

PREPARATION EXAMPLE 31

[Preparation of compound (18-1)]
Preparation of 3-amino-5-(2,6-dichloro-4-trifluoromethylphenyl)-1-methylpyrazole To a solution of 80 ml of ethanol and 80 ml of water was added 15.1 g of methylhydrazine with ice cooling, and a solution of 34.0 g of 3-(2,6-dichloro-4-trifluoromethyl)phenol-1,2-dibromopropionitrile (21) in 50 ml of ethanol was slowly added to the resulting mixture. The mixture was stirred at 0° C. for 1 hour and further stirred at 70° to 80° C. for 5 hours. The solvent was distilled off under reduced pressure to obtain a residue, to which brine was added. The mixture was extracted four times with a chloroform solution containing 10% of ethanol. The organic layers were washed with brine, dried over anhydrous magnesium sulfate and concentrated under reduced pressure to obtain a residue. Addition of dry ether to the residue gave 18.6 g of the desired compound in the form of a light brown solid (yield 75.0%).

$^1$H-NMR(CDCl$_3$, TMS, δ ppm): 3.42(s, 3H), 5.60(s, 1H), 7.61(s, 2H)

PREPARATION EXAMPLE 32

[Preparation of compound (1-13)]
Preparation of 5-(2,6-dichloro-4-trifluoromethylphenyl)-1-methyl-3-methylthiopyrazole (compound 33)

Methylhydrazine (1.9 g) was added dropwise to a solution of 5.0 g of 3,3-bis[methylthio]-1-(2,6-dichloro-4-trifluoromethylphenyl)-2-propen-1-one (22) in 50 ml of ethanol at room temperature, followed by refluxing for 3 hours. The solvent was distilled off under reduced pressure to obtain a residue, which was purified by column chromatography on silica gel, giving 1.6 g of the desired compound in the form of a brown oil (yield 28.5%).

$^1$H-NMR(CDCl$_3$, TMS, δ ppm): 2.63(s, 3H), 3.69(s, 3H), 6.24(s, 1H), 7.70(s, 2H)

PREPARATION EXAMPLE 33

Preparation of 5(3)-(2,6-dichloro-4-trifluoromethylphenyl)-3(5)-methylsulfenyl-4-methylpyrazole (compound 36)

Hydrazine monohydrate (0.51 ml) was added dropwise to a solution of 3.6 g of 3,3-bis[methylthio]-1-(2,6-dichloro-4-trifluoromethylphenyl)-2-methylpropen-1-one (22) in 40 ml of ethanol at room temperature, and the mixture was stirred for 45 minutes and thereafter refluxed for 4 hours. The reaction mixture was concentrated under reduced pressure to obtain a residue, which was purified by column chromatography on silica gel, giving 3.3 g of the desired compound in the form of a white solid (quantitative yield). m.p. 92°–95° C. $^1$H-NMR(CDCl$_3$, TMS, δ ppm): 1.94(s, 3H), 2.45(s, 3H), 6.41(s, 1H), 7.65(s, 2H), 10.61(br, 1H)

PREPARATION EXAMPLE 34

[Preparation of compound (47)]
Preparation of 5-(2,6-dichloro-4-trifluoromethylphenyl)-1-ethyl-3-methylsulfenylpyrazole To a suspension of 0.30 g of 60% oily sodium hydride in 10 ml of anhydrous tetrahydrofuran was added dropwise a suspension of 2.0 g of 5(3)-(2,6-dichloro-4-trifluoromethylphenyl)-3(5)-methylsulfenylpyrazole in 3 ml of anhydrous tetrahydrofuran, and the mixture was stirred at room temperature for 30 minutes. A tetrahydrofuran solution (2 ml) containing 1.5 g of iodoethane was added to the mixture at room temperature, followed by further stirring for 1 hour. The reaction mixture was poured into ice water, followed by extraction with ethyl acetate. The extracts were combined together, washed with brine and dried over anhydrous magnesium sulfate. The solvent was distilled off under reduced pressure to obtain a residue, which was then purified by column chromatography on silica gel, giving 0.56 g of the desired compound in the form of a colorless oil (yield 26.0%).

$^1$H-NMR(CDCl$_3$, TMS, δ ppm): 1.26(t, 3H), 2.47(s, 3H), 3.80(q, 2H), 6.11(s, 1H), 7.61(s, 2H)

PREPARATION EXAMPLE 32

Preparation of 3-amino-4-bromo-5-(2,6-dichloro-4-trifluoromethylphenyl)-1-methylpyrazole (intermediate)

Bromine (0.12 g) was added to a solution of 0.3 g of 3-amino-5-(2,6-dichloro-4-trifluoromethylphenyl)-1-methylpyrazole in 5 ml of anhydrous carbon tetrachloride at room temperature, and the mixture was stirred at room temperature for 10 minutes. The solvent was distilled off under reduced pressure to obtain a residue, which was then purified by column chromatography on silica gel (eluent: ether/hexane=1/5), affording 0.4 g of the desired compound in the form of white crystals (quantitative yield).

$^1$H-NMR(CDCl$_3$, TMS, δ ppm): 3.52(s, 3H), 3.78(br, 2H), 7.71(s, 2H).

PREPARATION EXAMPLE 36

[Preparation of compound (1-12)]
Preparation of 4-chloro-5-(2,6-dichloro-4-trifluoromethylphenyl)-3-methylthio-1-methylpyrazole (compound 42)

Dimethyl disulfide (0.14 ml) and 0.2 ml of tert-butyl nitrite were added dropwise to a solution of 0.2 g of 3-amino-4-chloro-5-(2,6-dichloro-4-trifluoromethylphenyl)-1-methylpyrazole (18) in 5 ml of dry methylene chloride with ice cooling. The mixture was stirred at 0° C. for 30 minutes and thereafter poured into water, followed by extraction with chloroform. The organic layer was washed with brine and dried over magnesium sulfate, and the solvent was distilled off under reduced pressure. The residue obtained was purified by column chromatography on silica gel, giving 0.2 g of the desired compound in the form of a light brown oil (quantitative yield).

$^1$H-NMR(CDCl$_3$, TMS, δ ppm): 2.56(s, 3H), 3.66(s, 3H), 7.73(s, 2H)

PREPARATION EXAMPLE 37

[Preparation of compound (1-15)]
Preparation of 5-(2,6-dichloro-4-trifluoromethylphenyl)-1-methyl-3-methylsulfinylpyrazole (compound 40)

To a solution of 0.3 g of 5-(2,6-dichloro-4-trifluoromethylphenyl)-1-methyl-3-methylsulfenylpyrazole (compound 33) in 20 ml of anhydrous chloroform was slowly added 0.3 g of 70% m-chloroperbenzoic acid at −10° C. with stirring, followed by stirring for 3 hours. The reaction mixture was poured into saturated aqueous sodium hydrogencarbonate solution, and the organic layer was separated off and washed with a 5% aqueous sodium hydroxide solution and with brine. After drying the layer over anhydrous magnesium sulfate, the solvent was distilled off under reduced pressure, giving 0.3 g of the desired compound in the form of white crystals (quantitative crude yield).

$^1$H-NMR(CDCl$_3$, TMS, δ ppm): 2.97(s, 3H), 3.74(s, 3H), 6.79(s, 1H), 7.71(s, 2H)

PREPARATION EXAMPLE 38

[Preparation of compound (1-16)]
Preparation of 5-(2,6-dichloro-4-trifluoromethylphenyl)-1-methyl-3-methylsulfonylpyrazole (compound 41)

To a solution of 0.2 g of 5-(2,6-dichloro-4-trifluoromethylphenyl)-1-methyl-3-methylsulfenylpyrazole (compound 40) in 20 ml of anhydrous chloroform was slowly added 0.3 g of 70% m-chloroperbenzoic acid at room temperature, followed by stirring overnight. The reaction mixture was poured into 10% aqueous sodium sulfite solution, and the organic layer was separated off, washed with 5% aqueous sodium hydroxide solution and brine and dried over anhydrous magnesium sulfate. The solvent was thereafter distilled of under reduced pressure to give 0.3 g of the desired compound in the form of white crystals (quantitative crude yield).

$^1$H-NMR(CDCl$_3$, TMS, δ ppm): 3.18(3H), 3.94(s, 3H), 6.91(s, 1H), 7.71(s, 2H)

Tables 3 and 4 show compounds of the invention prepared in the same manner as in the foregoing preparation examples.

TABLE 3

| Compound No | R$^1$ | R$^2$ | R$^3$ | n | $^1$H-NMR (CDCl$_3$, TMS, δ, ppm) | Property |
|---|---|---|---|---|---|---|
| 32 | Me | H | H | 0 | 3.90(s, 3H), 6.51(s, 1H), 7.62(s, 2H) | colorless oil |
| 33 | Me | Me | H | 0 | 2.63(s, 3H), 3.69(s, 3H), 6.24(s, 1H), 7.70(s, 2H) | brown oil |
| 34 | Me | Et | H | 0 | 0.99(t, 3H), 2.28(q, 2H), 3.59(s, 3H), 7.71(s, 2H) | light yellow oil |
| 35 | Me | n-Pr | H | 0 | 1.01(t, 3H), 1.70(q, 3H), 2.93(t, 2H), 3.63(s, 3H), 6.26(s, 1H), 7.69(s, 2H) | colorless oil |
| 36 | H | Me | Me | 0 | 1.94(s, 3H), 2.45(s, 3H), 7.67(s, 2H), 10.6(br, 1H) | light brown solid mp = 92–95° C. |
| 37 | Me | CH$_2$CH=CH$_2$ | H | 0 | 3.46–3.71(m, 5H), 4.98–5.31(m, 2H), 5.72–5.99(m, 1H), 6.30(s, 1H), 7.70(s, 2H) | light yellow oil |
| 38 | Me | CH$_2$Ph | H | 0 | 3.64(s, 3H), 4.14(s, 2H), 6.10(s, 1H), 7.26(s, 5H), 7.68(s, 2H) | brown oil |
| 39 | Me | Ph | H | 0 | 3.76(s, 3H), 6.79(s, 1H), 7.19–7.28(m, 5H), 7.71(s, 2H) | resin |
| 40 | Me | Me | H | 1 | 2.97(s, 3H), 3.74(s, 3H), 6.79(s, 1H), 7.71(s, 2H) | white solid mp = 92–95° C. |
| 41 | Me | Me | H | 2 | 3.18(s, 3H), 3.94(s, 3H), 6.91(s, 1H), 7.71(s, 2H) | white resin |

TABLE 4

| Compound No | R$^1$ | R$^2$ | R$^3$ | n | $^1$H-NMR (CDCl$_3$, TMS, δ, ppm) | Property |
|---|---|---|---|---|---|---|
| 42 | Me | Me | Cl | 0 | 2.56(s, 3H), 3.66(s, 3H), 7.73(s, 2H) | white solid mp = 65–66° C. |
| 43 | Me | Me | Br | 0 | 2.56(s, 3H), 3.67(s, 3H), 7.74(s, 2H) | white solid mp = 66–68° C. |
| 44 | Me | Me | I | 0 | 2.57(s, 3H), 3.70(s, 3H), 7.74(s, 2H) | white solid mp = 71–73° C. |
| 45 | Me | Me | Br | 2 | 3.27(s, 3H), 3.77(s, 3H), 7.75(s, 2H) | white solid mp = 108–110° C. |

TABLE 4-continued

| Compound No | $R^1$ | $R^2$ | $R^3$ | n | $^1$H-NMR (CDCl$_3$, TMS, δ, ppm) | Property |
|---|---|---|---|---|---|---|
| 46 | CH$_2$Ph | Me | H | 0 | 2.47(s, 3H), 5.42(br, 2H), 6.61(s, 1H), 7.20–7.67(m, 7H) | resin |
| 47 | Et | Me | H | 0 | 1.26(t, 3H), 2.47(s, 3H), 3.80(q, 2H), 6.11(s, 1H), 7.61(s, 2H) | colorless oil |
| 48 | n-Bu | Me | H | 0 | 0.85–2.10(m, 7H), 2.55(s, 3H), 3.80(t, 2H), 6.19(s, 1H), 7.71(s, 2H) | colorless resin |
| 49 | CH$_2$F | Me | H | 0 | 2.61(s, 3H), 5.73(d, 2H), 6.31(s, 1H), 7.71(s, 2H) | light yellow green resin |
| 50 | CF$_3$ | Me | H | 0 | 2.57(s, 3H), 6.35(s, 1H), 7.73(s, 2H) | yellow oil |
| 51 | Me | Me | Me | 0 | 2.51(s, 3H), 3.61(s, 3H), 7.71(s, 2H) | white solid mp = 62–64° C. |

Formulation Example 1

Emulsifiable concentrate

| Compound of the invention | 10 parts |
|---|---|
| Xylene | 35 parts |
| N,N-Dimethylformamide | 35 parts |
| Polyoxyethylene styrylphenyl ether | 14 parts |
| Calcium dodecylbenzenesulfonate | 6 parts |

The above ingredients were mixed together with stirring to obtain a 10% emulsifiable concentrate.

Formulation Example 2

Wettable powder

| Compound of the invention | 20 parts |
|---|---|
| Sodium lauryl sulfate | 4 parts |
| Lignosulfonic acid, calcium salt | 2 parts |
| Finely divided water—containing synthetic silicon oxide | 20 parts |
| Diatomite | 54 parts |

The above ingredients were mixed together with stirring using a juice mixer to obtain a 20% wettable powder.

Formulation Example 3

Granules

| Compound of the invention | 5 parts |
|---|---|
| Finely divided water—containing synthetic silicon oxide | 5 parts |
| Sodium dodecylbenzenesulfonate | 5 parts |
| Bentonite | 30 parts |
| Clay | 55 parts |

The above ingredients were mixed together, thoroughly stirred, further stirred with addition of a suitable amount of water and made into granules by a granulating machine, followed by drying in an air stream to obtain a 5% granular formulation.

Formulation Example 4

Dust

| Compound of the invention | 1 part |
|---|---|
| Finely divided water—containing synthetic silicon oxide | 5 parts |
| PAP | 0.3 part |
| Clay | 93.7 parts |

A solution of compound of the invention in a suitable amount of acetone was added to the other ingredients, the ingredients were mixed together by stirring in a juice mixer, and the acetone was thereafter evaporated off to obtain a 1% dust formulation.

Formulation Example 5

Suspension concentrate

Twenty parts of a compound of the invention and 1.5 parts of sorbitan trioleate were admixed with 28.5 parts of an aqueous solution containing 2 parts of polyvinyl alcohol, and the mixture was finely ground by a sand grinder to particle diameter of 3 μm or less. Xanthane gum (0.05 part) and 40 parts of an aqueous solution containing 0.1 part of aluminum magnesium silicate were added to the finely divided mixture, and the resulting mixture was further stirred with 10 parts of propylene glycol added thereto to obtain a 20% suspension concentrate.

Test Example 1

Insecticidal Test on *Laodelphax striatellus*

A 10% emulsiliable concentrate of the compound of the invention listed in Table 5 was diluted with water containing a wetting agent (aqueous solution containing 10% Tween 80) to prepare 10 ml of an insecticidal liquid composition, which was then applied to vinyl pots (7.5 cm in diameter) having planted therein paddy rice seedlings in 2.5-leaf stage. Each of the pots was thereafter covered with an acrylic resin cage, in which 10 female adults of *Laodelphax striatellus* were released. The pots thus prepared were placed in a chamber having a constant temperature of 25° C. and constant humidity of 40%, and checked for mortality two days later. The test was conducted on three pots. Table 5 shows the result.

Test Example 2

Insecticidal Test on *Plutella xylostella*

A 20% wettable preparation of the compound of the invention listed in Table 6 was diluted with water to prepare an insecticidal liquid composition having a concentration of 400 ppm. A cabbage leaf was dipped in the composition, then dried in an air stream and thereafter given to 10 fourth-instar larvae of *Plutella xylostella* within a plastic cup (8 cm in diameter and 4 cm in depth) having filter paper laid therein. The cup was then placed in a chamber having a constant temperature of 25° C. and constant humidity of 40%, and checked for mortality two days later. The test was conducted in three cups. Table 6 shows the result.

TABLE 5

| Compound | mortality | Compound | mortality |
|---|---|---|---|
| 1 | 100 | 11 | 100 |
| 2 | 100 | 23 | 100 |
| 3 | 100 | 25 | 100 |
| 4 | 100 | 34 | 100 |
| 5 | 100 | 35 | 100 |
| 6 | 100 | 41 | 100 |
| 7 | 100 | 48 | 100 |
| 8 | 100 | 49 | 100 |
| 9 | 100 | — | 0 |
| 10 | 100 | | |

TABLE 6

| Compound | mortality | Compound | mortality |
|---|---|---|---|
| 1 | 100 | 35 | 100 |
| 7 | 100 | 41 | 100 |
| 25 | 100 | 49 | 100 |
| 34 | 100 | — | 0 |

Test Example 3

Insecticidal Test on *Musca domestica*

An acetone solution of the compound of the invention listed in Tables 3 and 4 was adjusted to a specified concentration. The solution was applied to the back of the chest of female adults of *Musca domestica* in an amount of 0.5 μl for each insect using a microapplicator. Ten such adults were accommodated in a plastic container (10 cm in diameter) having placed therein absorbent cotton impregnated with a sucrose solution. The container was then allowed to stand within a chamber having a constant temperature of 25° C. and constant humidity of 40% and checked for mortality two days later. The test was conducted in three containers. As a result, the compounds of the invention, Nos. 34, 35, 41, 48 and 49 achieved a mortality of 100%.

INDUSTRIAL APPLICABILITY

The compounds of the invention exhibit high insecticidal activity on a wide variety of agricultural pest insects but produce almost no injury to mammals, fishes and beneficial insects. Accordingly, the compounds of the invention provide useful compositions for controlling harmful organisms.

We claim:

1. A pyrazole derivative represented by the formula (1)

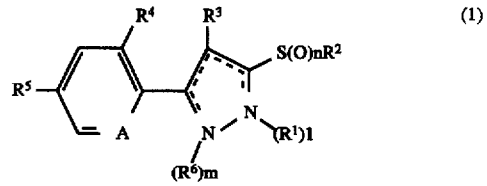

wherein A is CH, N or C-halogen atom, $R^1$ is hydrogen atom, lower alkyl, lower haloalkyl, benzyl or phenyl, $R^2$ is lower alkyl, lower haloalkyl, lower alkenyl, lower alkynyl, benzyl or phenyl, $R^3$ is hydrogen atom, a halogen atom lower alkyl, lower haloalkylthio, phenyl, cyano, nitro or amino, $R^4$ is halogen atom, $R^5$ is lower haloalkyl, $R^6$ is hydrogen atom, lower alkyl, lower haloalkyl or benzyl, l is 0 or 1, m is 0 or 1, the total of l and m is 1, and n is a number of 0 to 2.

2. A pyrazole derivative as defined in claim 1 which is represented by the formula (1A)

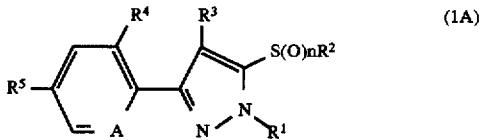

wherein A and $R^1$ to $R^5$ are the same as above.

3. A pyrazole derivative as defined in claim 1 which is represented by the formula (1B)

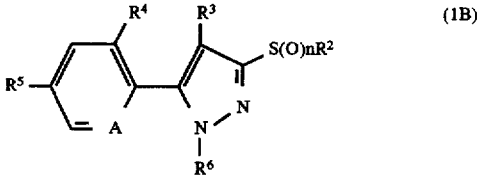

wherein A and $R^2$ to $R^6$ are the same as above.

4. A compound as defined in claim 1 wherein A is C—Cl.
5. A compound as defined in claim 2 wherein A is C—Cl.
6. A compound as defined in claim 3 wherein A is C—Cl.
7. A compound as defined in claim 1 wherein $R^5$ is trifluoromethyl.
8. A compound as defined in claim 2 wherein $R^5$ is trifluoromethyl.
9. A compound as defined in claim 3 wherein $R^5$ is trifluoromethyl.
10. An insecticidal composition comprising at least one pyrazole derivative of claim 1 as its active component.
11. An insecticidal composition comprising at least one pyrazole derivative of claim 2 as its active component.
12. An insecticidal composition comprising at least one pyrazole derivative of claim 3 as its active component.

* * * * *